(12) United States Patent
Jacobson et al.

(10) Patent No.: US 9,168,383 B2
(45) Date of Patent: *Oct. 27, 2015

(54) LEADLESS CARDIAC PACEMAKER WITH CONDUCTED COMMUNICATION

(75) Inventors: Peter M. Jacobson, Livermore, CA (US); Alan Ostroff, Pleasanton, CA (US); Timothy E. Ciciarelli, San Jose, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 7 days.

This patent is subject to a terminal disclaimer.

(21) Appl. No.: 13/277,151

(22) Filed: Oct. 19, 2011

(65) Prior Publication Data

US 2012/0109236 A1     May 3, 2012

Related U.S. Application Data

(63) Continuation-in-part of application No. 13/109,728, filed on May 17, 2011, now Pat. No. 8,295,939, which is a continuation of application No. 11/549,605, filed on Oct. 13, 2006, now Pat. No. 7,945,333, application (Continued)

(51) Int. Cl.
*A61N 1/00* (2006.01)
*A61N 1/372* (2006.01)
(Continued)

(52) U.S. Cl.
CPC .............. *A61N 1/3727* (2013.01); *A61N 1/368* (2013.01); *A61N 1/3756* (2013.01); *A61N 1/37217* (2013.01); *A61N 1/37288* (2013.01); *A61N 1/3684* (2013.01); *A61N 1/37205* (2013.01)

USPC .............................................. 607/32; 607/60

(58) Field of Classification Search
CPC ... A61N 1/368; A61N 1/37288; A61N 1/356; A61N 1/3727; A61N 1/3756; A61N 1/37217; A61N 1/375; A61N 1/37252; A61N 1/37276
USPC ................................................ 607/32–33, 60
See application file for complete search history.

(56) References Cited

U.S. PATENT DOCUMENTS

| | | |
|---|---|---|
| 3,199,508 A | 8/1965 | Roth |
| 3,212,496 A | 10/1965 | Preston |
| 3,218,638 A | 11/1965 | Honig |

(Continued)

FOREIGN PATENT DOCUMENTS

| | | |
|---|---|---|
| EP | 13277151 120 | 0/3762 |
| EP | 1741465 A1 | 1/2007 |

(Continued)

OTHER PUBLICATIONS

U.S. Appl. No. 10/891,747 entitled "System and method for synchronizing supplemental pacing pulses generated by a satellite pacing device with primary pulses delivered by a separate pacing device," filed Jul. 14, 2004 (abandoned prior to pub.: CIP of this app. is U.S. Pat. 7,630,767).

(Continued)

*Primary Examiner* — Catherine Voorhees
(74) *Attorney, Agent, or Firm* — Theresa A. Raymer

(57) ABSTRACT

A leadless pacemaker for pacing a heart of a human includes a hermetic housing and at least two electrodes on or near the hermetic housing. The at least two electrodes are configured to deliver energy to stimulate the heart and to transfer information to or from at least one external device.

34 Claims, 16 Drawing Sheets

Related U.S. Application Data

No. 13/277,151, which is a continuation-in-part of application No. 13/098,266, filed on Apr. 29, 2011, which is a continuation of application No. 11/549,603, filed on Oct. 13, 2006, now Pat. No. 7,937,148.

(60) Provisional application No. 60/726,706, filed on Oct. 14, 2005, provisional application No. 60/761,531, filed on Jan. 24, 2006, provisional application No. 60/729,671, filed on Oct. 24, 2005, provisional application No. 60/737,296, filed on Nov. 16, 2005, provisional application No. 60/739,901, filed on Nov. 26, 2005, provisional application No. 60/749,017, filed on Dec. 10, 2005, provisional application No. 60/761,740, filed on Jan. 24, 2006.

(51) Int. Cl.
*A61N 1/368* (2006.01)
*A61N 1/375* (2006.01)

(56) References Cited

U.S. PATENT DOCUMENTS

| | | |
|---|---|---|
| 3,241,556 A | 3/1966 | Zacouto |
| 3,478,746 A | 11/1969 | Greatbatch |
| 3,603,881 A | 9/1971 | Thornton |
| 3,727,616 A | 4/1973 | Lenzkes |
| 3,757,778 A | 9/1973 | Graham |
| 3,823,708 A | 7/1974 | Lawhorn |
| 3,830,228 A | 8/1974 | Foner |
| 3,835,864 A | 9/1974 | Rasor et al. |
| 3,836,798 A | 9/1974 | Greatbatch |
| 3,870,051 A | 3/1975 | Brindley |
| 3,872,251 A | 3/1975 | Auerbach et al. |
| 3,905,364 A | 9/1975 | Cudahy et al. |
| 3,940,692 A | 2/1976 | Neilson et al. |
| 3,943,926 A | 3/1976 | Barragan |
| 3,946,744 A | 3/1976 | Auerbach |
| 3,952,750 A | 4/1976 | Mirowski et al. |
| 4,027,663 A | 6/1977 | Fischler et al. |
| 4,072,154 A | 2/1978 | Anderson et al. |
| 4,083,366 A | 4/1978 | Gombrich et al. |
| 4,087,389 A | 5/1978 | Coppola |
| 4,102,344 A | 7/1978 | Conway et al. |
| 4,146,029 A | 3/1979 | Ellinwood, Jr. |
| 4,151,513 A | 4/1979 | Menken et al. |
| 4,151,540 A | 4/1979 | Sander et al. |
| 4,152,540 A | 5/1979 | Duncan et al. |
| 4,173,221 A | 11/1979 | McLaughlin et al. |
| 4,187,854 A | 2/1980 | Hepp et al. |
| 4,210,149 A | 7/1980 | Heilman et al. |
| RE30,366 E | 8/1980 | Rasor et al. |
| 4,223,678 A | 9/1980 | Langer et al. |
| 4,250,888 A | 2/1981 | Grosskopf |
| 4,256,115 A | 3/1981 | Bilitch |
| 4,296,756 A | 10/1981 | Dunning et al. |
| 4,310,000 A | 1/1982 | Lindemans |
| 4,312,354 A | 1/1982 | Walters |
| 4,318,412 A | 3/1982 | Stanly et al. |
| 4,336,810 A | 6/1982 | Anderson et al. |
| 4,350,169 A | 9/1982 | Dutcher et al. |
| 4,374,382 A | 2/1983 | Markowitz |
| 4,406,288 A | 9/1983 | Horwinski et al. |
| 4,411,271 A | 10/1983 | Markowitz |
| 4,418,695 A | 12/1983 | Buffet |
| 4,424,551 A | 1/1984 | Stevenson et al. |
| 4,428,378 A | 1/1984 | Anderson et al. |
| 4,440,173 A | 4/1984 | Hudziak et al. |
| 4,442,840 A | 4/1984 | Wojciechowicz, Jr. |
| 4,453,162 A | 6/1984 | Money et al. |
| 4,481,950 A | 11/1984 | Duggan |
| 4,513,743 A | 4/1985 | van Arragon et al. |
| 4,516,579 A | 5/1985 | Irnich |
| 4,522,208 A | 6/1985 | Buffet |
| 4,524,774 A | 6/1985 | Hildebrandt |
| 4,531,527 A | 7/1985 | Reinhold, Jr. et al. |
| 4,543,955 A | 10/1985 | Schroeppel |
| 4,550,370 A | 10/1985 | Baker |
| 4,552,127 A | 11/1985 | Schiff |
| 4,552,154 A | 11/1985 | Hartlaub |
| 4,562,846 A | 1/1986 | Cox et al. |
| 4,586,508 A | 5/1986 | Batina et al. |
| 4,606,352 A | 8/1986 | Geddes et al. |
| 4,607,639 A | 8/1986 | Tanagho et al. |
| 4,612,934 A | 9/1986 | Borkan |
| 4,625,730 A | 12/1986 | Fountain et al. |
| 4,679,144 A | 7/1987 | Cox et al. |
| 4,681,111 A | 7/1987 | Silvian |
| 4,681,117 A | 7/1987 | Brodman et al. |
| 4,702,253 A | 10/1987 | Nappholz et al. |
| 4,719,920 A | 1/1988 | Alt et al. |
| 4,722,342 A | 2/1988 | Amundson |
| 4,750,495 A | 6/1988 | Moore et al. |
| 4,763,340 A | 8/1988 | Yoneda et al. |
| 4,763,655 A | 8/1988 | Wirtzfeld et al. |
| 4,787,389 A | 11/1988 | Tarjan |
| 4,791,931 A | 12/1988 | Slate |
| 4,793,353 A | 12/1988 | Borkan |
| 4,794,532 A | 12/1988 | Leckband et al. |
| 4,802,481 A | 2/1989 | Schroeppel |
| 4,809,697 A | 3/1989 | Causey, III et al. |
| 4,827,940 A | 5/1989 | Mayer et al. |
| 4,830,006 A | 5/1989 | Haluska et al. |
| 4,844,076 A | 7/1989 | Lesho et al. |
| 4,846,195 A | 7/1989 | Alt |
| 4,858,610 A | 8/1989 | Callaghan et al. |
| 4,860,750 A | 8/1989 | Frey et al. |
| 4,875,483 A | 10/1989 | Vollmann et al. |
| 4,880,004 A | 11/1989 | Baker, Jr. et al. |
| 4,883,064 A | 11/1989 | Olson et al. |
| 4,886,064 A | 12/1989 | Strandberg |
| 4,896,068 A | 1/1990 | Nilsson |
| 4,903,701 A | 2/1990 | Moore et al. |
| 4,905,708 A | 3/1990 | Davies |
| 4,926,863 A | 5/1990 | Alt |
| 4,974,589 A | 12/1990 | Sholder |
| 4,987,897 A | 1/1991 | Funke |
| 4,995,390 A | 2/1991 | Cook et al. |
| 5,010,887 A | 4/1991 | Thornander |
| 5,012,806 A | 5/1991 | De Bellis |
| 5,014,701 A | 5/1991 | Pless et al. |
| 5,040,533 A | 8/1991 | Fearnot |
| 5,040,534 A | 8/1991 | Mann et al. |
| 5,040,536 A | 8/1991 | Riff |
| 5,042,497 A | 8/1991 | Shapland |
| 5,052,399 A | 10/1991 | Olive et al. |
| 5,058,581 A | 10/1991 | Silvian |
| 5,065,759 A | 11/1991 | Begemann |
| 5,076,270 A | 12/1991 | Stutz, Jr. |
| 5,076,272 A | 12/1991 | Ferek-Petric |
| 5,085,224 A | 2/1992 | Galen et al. |
| 5,086,772 A | 2/1992 | Larnard et al. |
| 5,088,488 A | 2/1992 | Markowitz et al. |
| 5,095,903 A | 3/1992 | DeBellis |
| 5,109,845 A | 5/1992 | Yuuchi et al. |
| 5,111,816 A | 5/1992 | Pless et al. |
| 5,113,859 A * | 5/1992 | Funke ............................ 607/4 |
| 5,113,869 A | 5/1992 | Nappholz et al. |
| 5,133,350 A | 7/1992 | Duffin |
| 5,135,004 A | 8/1992 | Adams et al. |
| 5,170,784 A | 12/1992 | Ramon et al. |
| 5,170,802 A | 12/1992 | Mehra |
| 5,179,947 A | 1/1993 | Meyerson et al. |
| 5,184,616 A | 2/1993 | Weiss |
| 5,193,539 A | 3/1993 | Schulman et al. |
| 5,193,540 A | 3/1993 | Schulman et al. |
| 5,193,550 A | 3/1993 | Duffin |
| 5,217,010 A | 6/1993 | Tsitlik et al. |
| 5,247,945 A | 9/1993 | Heinze et al. |
| 5,259,394 A | 11/1993 | Bens |
| 5,260,621 A | 11/1993 | Little et al. |
| 5,267,150 A | 11/1993 | Wilkinson |
| 5,282,841 A | 2/1994 | Szyszkowski |

(56) References Cited

U.S. PATENT DOCUMENTS

| | | |
|---|---|---|
| 5,284,136 A | 2/1994 | Hauck et al. |
| 5,291,902 A | 3/1994 | Carman |
| 5,300,093 A | 4/1994 | Koestner et al. |
| 5,304,206 A | 4/1994 | Baker, Jr. et al. |
| 5,304,209 A | 4/1994 | Adams et al. |
| 5,313,953 A | 5/1994 | Yomtov et al. |
| 5,318,596 A | 6/1994 | Barreras et al. |
| 5,331,966 A | 7/1994 | Bennett et al. |
| 5,333,095 A | 7/1994 | Stevenson et al. |
| 5,336,244 A | 8/1994 | Weijand |
| 5,342,401 A | 8/1994 | Spano et al. |
| 5,354,317 A | 10/1994 | Alt |
| 5,358,514 A | 10/1994 | Schulman et al. |
| 5,373,852 A | 12/1994 | Harrison et al. |
| 5,383,912 A | 1/1995 | Cox et al. |
| 5,383,915 A | 1/1995 | Adams |
| 5,404,877 A | 4/1995 | Nolan et al. |
| 5,405,367 A | 4/1995 | Schulman et al. |
| 5,406,444 A | 4/1995 | Selfried et al. |
| 5,411,532 A | 5/1995 | Mortazavi |
| 5,411,535 A | 5/1995 | Fujii |
| 5,411,537 A | 5/1995 | Munshi et al. |
| 5,417,222 A | 5/1995 | Dempsey et al. |
| 5,419,337 A | 5/1995 | Dempsey et al. |
| 5,431,171 A | 7/1995 | Harrison et al. |
| 5,446,447 A | 8/1995 | Carney et al. |
| 5,456,261 A | 10/1995 | Luczyk |
| 5,466,246 A | 11/1995 | Silvian |
| 5,469,857 A | 11/1995 | Laurent et al. |
| 5,480,415 A | 1/1996 | Cox et al. |
| 5,481,262 A | 1/1996 | Urbas et al. |
| 5,522,876 A | 6/1996 | Rusink |
| 5,531,779 A | 7/1996 | Dahl et al. |
| 5,531,781 A | 7/1996 | Alferness et al. |
| 5,531,783 A | 7/1996 | Giele et al. |
| 5,539,775 A | 7/1996 | Tuttle et al. |
| 5,549,654 A | 8/1996 | Powell |
| 5,549,659 A | 8/1996 | Johansen et al. |
| 5,551,427 A | 9/1996 | Altman |
| 5,556,421 A | 9/1996 | Prutchi et al. |
| 5,562,717 A | 10/1996 | Tippey et al. |
| 5,571,143 A | 11/1996 | Hoegnelid et al. |
| 5,571,148 A | 11/1996 | Loeb et al. |
| 5,579,775 A | 12/1996 | Dempsey et al. |
| 5,586,556 A | 12/1996 | Spivey et al. |
| 5,591,217 A | 1/1997 | Barreras |
| 5,598,848 A | 2/1997 | Swanson et al. |
| 5,649,952 A | 7/1997 | Lam |
| 5,650,759 A | 7/1997 | Hittman et al. |
| 5,654,984 A | 8/1997 | Hershbarger et al. |
| 5,662,689 A | 9/1997 | Elsberry et al. |
| 5,669,391 A | 9/1997 | Williams |
| 5,674,259 A | 10/1997 | Gray |
| 5,676,153 A | 10/1997 | Smith et al. |
| 5,693,076 A | 12/1997 | Kaemmerer |
| 5,694,940 A | 12/1997 | Unger et al. |
| 5,694,952 A | 12/1997 | Lidman et al. |
| 5,697,958 A | 12/1997 | Paul et al. |
| 5,702,427 A | 12/1997 | Ecker et al. |
| 5,725,559 A | 3/1998 | Alt et al. |
| 5,728,154 A | 3/1998 | Crossett et al. |
| 5,730,143 A | 3/1998 | Schwarzberg |
| 5,735,880 A | 4/1998 | Prutchi et al. |
| 5,738,102 A | 4/1998 | Lemelson |
| 5,740,811 A | 4/1998 | Hedberg et al. |
| 5,741,314 A | 4/1998 | Daly et al. |
| 5,766,231 A | 6/1998 | Erickson et al. |
| 5,792,202 A | 8/1998 | Rueter |
| 5,792,205 A | 8/1998 | Alt et al. |
| 5,810,735 A | 9/1998 | Halperin et al. |
| 5,814,076 A | 9/1998 | Brownlee |
| 5,814,087 A | 9/1998 | Renirie |
| 5,814,089 A | 9/1998 | Stokes et al. |
| 5,824,016 A | 10/1998 | Ekwall |
| 5,871,451 A | 2/1999 | Unger et al. |
| 5,876,353 A | 3/1999 | Riff |
| 5,876,425 A | 3/1999 | Gord et al. |
| 5,891,178 A | 4/1999 | Mann et al. |
| 5,899,928 A | 5/1999 | Sholder et al. |
| 5,935,079 A | 8/1999 | Swanson et al. |
| 5,954,761 A | 9/1999 | Machek et al. |
| 5,957,861 A | 9/1999 | Combs et al. |
| 5,984,861 A | 11/1999 | Crowley |
| 5,987,352 A | 11/1999 | Klein et al. |
| 5,995,876 A | 11/1999 | Kruse et al. |
| 5,999,857 A | 12/1999 | Weijand et al. |
| 6,002,969 A | 12/1999 | Machek et al. |
| 6,004,269 A | 12/1999 | Crowley et al. |
| 6,061,596 A | 5/2000 | Richmond et al. |
| 6,076,016 A | 6/2000 | Feierbach |
| 6,080,187 A | 6/2000 | Alt et al. |
| 6,093,146 A | 7/2000 | Filangeri |
| 6,096,065 A | 8/2000 | Crowley |
| 6,102,874 A | 8/2000 | Stone et al. |
| 6,112,116 A | 8/2000 | Fischell et al. |
| 6,115,628 A | 9/2000 | Stadler et al. |
| 6,115,630 A | 9/2000 | Stadler et al. |
| 6,115,636 A | 9/2000 | Ryan |
| 6,119,031 A | 9/2000 | Crowley |
| 6,125,290 A | 9/2000 | Miesel |
| 6,125,291 A | 9/2000 | Miesel et al. |
| 6,128,526 A | 10/2000 | Stadler et al. |
| 6,129,751 A | 10/2000 | Lucchesi et al. |
| 6,132,390 A | 10/2000 | Cookston et al. |
| 6,132,456 A | 10/2000 | Sommer et al. |
| 6,134,459 A | 10/2000 | Roberts et al. |
| 6,134,470 A | 10/2000 | Hartlaub |
| 6,139,510 A | 10/2000 | Palermo |
| 6,141,584 A | 10/2000 | Rockwell et al. |
| 6,141,588 A | 10/2000 | Cox et al. |
| 6,141,592 A | 10/2000 | Pauly |
| 6,144,866 A | 11/2000 | Miesel et al. |
| 6,148,230 A | 11/2000 | KenKnight |
| 6,152,882 A | 11/2000 | Prutchi |
| 6,163,723 A | 12/2000 | Roberts et al. |
| 6,164,284 A | 12/2000 | Schulman et al. |
| 6,167,310 A | 12/2000 | Grevious |
| 6,178,349 B1 | 1/2001 | Kieval |
| 6,178,356 B1 | 1/2001 | Chastain et al. |
| 6,185,443 B1 | 2/2001 | Crowley |
| 6,185,452 B1 | 2/2001 | Schulman et al. |
| 6,185,464 B1 | 2/2001 | Bonner et al. |
| 6,188,932 B1 | 2/2001 | Lindegren |
| 6,190,324 B1 | 2/2001 | Kieval et al. |
| 6,198,952 B1 | 3/2001 | Miesel |
| 6,201,993 B1 | 3/2001 | Kruse et al. |
| 6,208,894 B1 | 3/2001 | Schulman et al. |
| 6,208,900 B1 | 3/2001 | Ecker et al. |
| 6,223,081 B1 | 4/2001 | Kerver |
| 6,230,059 B1 | 5/2001 | Duffin |
| 6,236,882 B1 | 5/2001 | Lee et al. |
| 6,240,321 B1 | 5/2001 | Janke et al. |
| 6,243,608 B1 | 6/2001 | Pauly et al. |
| 6,248,080 B1 | 6/2001 | Miesel et al. |
| 6,263,245 B1 | 7/2001 | Snell |
| 6,265,100 B1 | 7/2001 | Saaski et al. |
| 6,266,554 B1 | 7/2001 | Hsu et al. |
| 6,266,564 B1 | 7/2001 | Hill et al. |
| 6,272,379 B1 | 8/2001 | Fischell et al. |
| 6,280,409 B1 | 8/2001 | Stone et al. |
| 6,289,229 B1 | 9/2001 | Crowley |
| 6,306,088 B1 | 10/2001 | Krausman et al. |
| 6,310,960 B1 | 10/2001 | Saaski et al. |
| 6,315,721 B2 | 11/2001 | Schulman et al. |
| 6,324,418 B1 | 11/2001 | Crowley et al. |
| 6,324,421 B1 | 11/2001 | Stadler et al. |
| RE37,463 E | 12/2001 | Altman |
| 6,343,227 B1 | 1/2002 | Crowley |
| 6,343,233 B1 | 1/2002 | Werner et al. |
| 6,347,245 B1 * | 2/2002 | Lee et al. ............... 600/523 |
| 6,358,202 B1 | 3/2002 | Arent |
| 6,361,522 B1 | 3/2002 | Scheiner et al. |
| 6,363,282 B1 | 3/2002 | Nichols et al. |
| 6,364,831 B1 | 4/2002 | Crowley |

(56) References Cited

U.S. PATENT DOCUMENTS

| | | |
|---|---|---|
| 6,370,434 B1 | 4/2002 | Zhang et al. |
| 6,381,492 B1 | 4/2002 | Rockwell et al. |
| 6,381,493 B1 | 4/2002 | Stadler et al. |
| 6,381,494 B1 | 4/2002 | Gilkerson et al. |
| 6,383,209 B1 | 5/2002 | Crowley |
| 6,385,593 B2 | 5/2002 | Linberg |
| 6,386,882 B1 | 5/2002 | Linberg |
| 6,397,100 B2 | 5/2002 | Stadler et al. |
| 6,402,689 B1 | 6/2002 | Scarantino et al. |
| 6,405,073 B1 | 6/2002 | Crowley et al. |
| 6,405,083 B1 | 6/2002 | Rockwell et al. |
| 6,409,674 B1 | 6/2002 | Brockway et al. |
| 6,409,675 B1 | 6/2002 | Turcott |
| 6,412,490 B1 | 7/2002 | Lee |
| 6,418,346 B1 | 7/2002 | Nelson et al. |
| 6,423,056 B1 | 7/2002 | Ishikawa et al. |
| 6,424,866 B2 | 7/2002 | Mika et al. |
| 6,428,484 B1 | 8/2002 | Battmer et al. |
| 6,434,429 B1 | 8/2002 | Kraus et al. |
| 6,438,410 B2 | 8/2002 | Hsu et al. |
| 6,438,417 B1 | 8/2002 | Rockwell et al. |
| 6,442,433 B1 | 8/2002 | Linberg |
| 6,444,970 B1 | 9/2002 | Barbato |
| 6,445,953 B1 | 9/2002 | Bulkes et al. |
| 6,458,145 B1 | 10/2002 | Ravenscroft et al. |
| 6,459,928 B2 | 10/2002 | Mika et al. |
| 6,459,937 B1 | 10/2002 | Morgan et al. |
| 6,466,820 B1 | 10/2002 | Juran et al. |
| 6,468,263 B1 | 10/2002 | Fischell et al. |
| 6,470,215 B1 | 10/2002 | Kraus et al. |
| 6,471,645 B1 | 10/2002 | Warkentin et al. |
| 6,472,991 B1 | 10/2002 | Schulman et al. |
| 6,477,424 B1 | 11/2002 | Thompson et al. |
| 6,480,733 B1 | 11/2002 | Turcott |
| 6,482,154 B1 | 11/2002 | Haubrich et al. |
| 6,484,055 B1 | 11/2002 | Marcovecchio |
| 6,484,057 B2 | 11/2002 | Ideker et al. |
| 6,490,487 B1 | 12/2002 | Kraus et al. |
| 6,496,715 B1 | 12/2002 | Lee et al. |
| 6,498,951 B1 | 12/2002 | Larson et al. |
| 6,500,168 B1 | 12/2002 | Jellie |
| 6,501,983 B1 | 12/2002 | Natarajan et al. |
| 6,512,949 B1 | 1/2003 | Combs et al. |
| 6,512,959 B1 | 1/2003 | Gomperz et al. |
| 6,522,926 B1 | 2/2003 | Kieval et al. |
| 6,522,928 B2 | 2/2003 | Whitehurst et al. |
| 6,539,257 B1 | 3/2003 | KenKnight |
| 6,542,781 B1 | 4/2003 | Koblish et al. |
| 6,556,860 B1 | 4/2003 | Groenewegen |
| 6,558,321 B1 | 5/2003 | Burd et al. |
| 6,564,807 B1 | 5/2003 | Schulman et al. |
| 6,567,680 B2 | 5/2003 | Swetlik et al. |
| 6,571,120 B2 | 5/2003 | Hutten |
| 6,574,509 B1 | 6/2003 | Kraus et al. |
| 6,574,511 B2 | 6/2003 | Lee |
| 6,580,946 B2 | 6/2003 | Struble |
| 6,580,948 B2 | 6/2003 | Haupert et al. |
| 6,584,351 B1 | 6/2003 | Ekwall |
| 6,584,352 B2 | 6/2003 | Combs et al. |
| 6,589,187 B1 | 7/2003 | Dimberger et al. |
| 6,592,518 B2 | 7/2003 | Denker et al. |
| 6,594,523 B1 | 7/2003 | Levine |
| 6,597,948 B1 | 7/2003 | Rockwell et al. |
| 6,597,952 B1 | 7/2003 | Mika et al. |
| 6,609,023 B1 | 8/2003 | Fischell et al. |
| 6,611,710 B2 | 8/2003 | Gomperz et al. |
| 6,615,075 B2 | 9/2003 | Mlynash et al. |
| 6,622,043 B1 | 9/2003 | Kraus et al. |
| 6,647,292 B1 | 11/2003 | Bardy et al. |
| 6,648,823 B2 | 11/2003 | Thompson |
| 6,649,078 B2 | 11/2003 | Yu |
| 6,654,638 B1 | 11/2003 | Sweeney |
| 6,658,285 B2 | 12/2003 | Potse et al. |
| 6,658,297 B2 | 12/2003 | Loeb |
| 6,658,301 B2 | 12/2003 | Loeb et al. |
| 6,659,959 B2 | 12/2003 | Brockway et al. |
| 6,669,631 B2 | 12/2003 | Norris et al. |
| 6,681,135 B1 | 1/2004 | Davis et al. |
| 6,684,100 B1 | 1/2004 | Sweeney et al. |
| 6,687,540 B2 | 2/2004 | Marcovecchio |
| 6,687,546 B2 | 2/2004 | Lebel et al. |
| 6,689,117 B2 | 2/2004 | Sweeney et al. |
| 6,690,959 B2 | 2/2004 | Thompson |
| 6,694,191 B2 | 2/2004 | Starkweather et al. |
| 6,695,885 B2 | 2/2004 | Schulman et al. |
| 6,697,672 B2 | 2/2004 | Andersson |
| 6,697,677 B2 | 2/2004 | Dahl et al. |
| 6,699,200 B2 | 3/2004 | Cao et al. |
| 6,702,857 B2 | 3/2004 | Brauker et al. |
| 6,704,602 B2 | 3/2004 | Berg et al. |
| 6,711,440 B2 | 3/2004 | Deal et al. |
| 6,716,238 B2 | 4/2004 | Elliott |
| 6,721,597 B1 | 4/2004 | Bardy et al. |
| 6,728,572 B2 | 4/2004 | Hsu et al. |
| 6,728,574 B2 | 4/2004 | Ujhelyi et al. |
| 6,728,576 B2 * | 4/2004 | Thompson et al. ............ 607/30 |
| 6,731,976 B2 | 5/2004 | Penn et al. |
| 6,731,979 B2 | 5/2004 | MacDonald |
| 6,733,485 B1 | 5/2004 | Whitehurst et al. |
| 6,735,474 B1 | 5/2004 | Loeb et al. |
| 6,735,475 B1 | 5/2004 | Whitehurst et al. |
| 6,738,670 B1 | 5/2004 | Almendinger et al. |
| 6,741,877 B1 | 5/2004 | Shults et al. |
| 6,741,886 B2 | 5/2004 | Yonce |
| 6,746,404 B2 | 6/2004 | Schwartz |
| 6,754,538 B2 | 6/2004 | Linberg |
| 6,760,620 B2 | 7/2004 | Sippens Groenewegen |
| 6,764,446 B2 | 7/2004 | Wolinsky et al. |
| 6,768,923 B2 | 7/2004 | Ding et al. |
| 6,783,499 B2 | 8/2004 | Schwartz |
| 6,785,576 B2 | 8/2004 | Verness |
| 6,786,860 B2 | 9/2004 | Maltan et al. |
| 6,792,314 B2 | 9/2004 | Byers et al. |
| 6,799,069 B2 | 9/2004 | Weiner et al. |
| 6,804,559 B1 | 10/2004 | Kraus et al. |
| 6,804,561 B2 | 10/2004 | Stover |
| 6,809,507 B2 | 10/2004 | Morgan et al. |
| 6,811,533 B2 | 11/2004 | Lebel et al. |
| 6,813,519 B2 | 11/2004 | Lebel et al. |
| 6,821,154 B1 | 11/2004 | Canfield et al. |
| 6,823,217 B2 | 11/2004 | Rutten et al. |
| 6,824,512 B2 | 11/2004 | Warkentin et al. |
| 6,829,508 B2 | 12/2004 | Schulman et al. |
| 6,839,596 B2 | 1/2005 | Nelson et al. |
| 6,848,052 B2 | 1/2005 | Hamid et al. |
| 6,850,801 B2 | 2/2005 | Kieval et al. |
| 6,856,835 B2 * | 2/2005 | Bardy et al. ............ 607/14 |
| 6,862,465 B2 | 3/2005 | Shults et al. |
| 6,862,480 B2 | 3/2005 | Cohen et al. |
| 6,865,420 B1 | 3/2005 | Kroll |
| 6,869,404 B2 | 3/2005 | Schulhauser et al. |
| 6,871,099 B1 | 3/2005 | Whitehurst et al. |
| 6,878,112 B2 | 4/2005 | Linberg et al. |
| 6,879,695 B2 | 4/2005 | Maltan et al. |
| 6,879,855 B2 | 4/2005 | Schulman et al. |
| 6,882,875 B1 | 4/2005 | Crowley |
| 6,889,081 B2 | 5/2005 | Hsu |
| 6,893,395 B1 | 5/2005 | Kraus et al. |
| 6,895,279 B2 | 5/2005 | Loeb et al. |
| 6,895,281 B1 | 5/2005 | Amundson et al. |
| 6,896,651 B2 | 5/2005 | Gross et al. |
| 6,897,788 B2 | 5/2005 | Khair et al. |
| 6,901,294 B1 | 5/2005 | Whitehurst et al. |
| 6,901,296 B1 | 5/2005 | Whitehurst et al. |
| 6,907,285 B2 | 6/2005 | Denker et al. |
| 6,907,293 B2 | 6/2005 | Grill et al. |
| 6,912,420 B2 | 6/2005 | Scheiner et al. |
| 6,917,833 B2 | 7/2005 | Denker et al. |
| 6,925,328 B2 | 8/2005 | Foster et al. |
| 6,931,327 B2 | 8/2005 | Goode, Jr. et al. |
| 6,999,821 B2 | 2/2006 | Jenney et al. |
| 7,001,372 B2 | 2/2006 | Richter |
| 7,023,359 B2 | 4/2006 | Goetz et al. |
| 7,146,222 B2 | 12/2006 | Boling |

(56) References Cited

U.S. PATENT DOCUMENTS

| | | |
|---|---|---|
| 7,146,225 B2 | 12/2006 | Guenst et al. |
| 7,164,950 B2 | 1/2007 | Kroll et al. |
| 7,181,505 B2 | 2/2007 | Haller et al. |
| 7,187,971 B2 | 3/2007 | Sommer et al. |
| 7,200,437 B1 | 4/2007 | Nabutovsky et al. |
| 7,212,870 B1 | 5/2007 | Helland |
| 7,277,754 B2 * | 10/2007 | McCabe et al. ............... 607/9 |
| 7,289,853 B1 | 10/2007 | Campbell et al. |
| 7,363,090 B2 | 4/2008 | Halperin et al. |
| 7,558,631 B2 | 7/2009 | Cowan et al. |
| 7,565,195 B1 | 7/2009 | Kroll et al. |
| 7,616,991 B2 | 11/2009 | Mann et al. |
| 7,630,767 B1 | 12/2009 | Poore et al. |
| 7,634,313 B1 | 12/2009 | Kroll et al. |
| 7,650,186 B2 | 1/2010 | Hastings et al. |
| 7,848,823 B2 | 12/2010 | Drasler et al. |
| 7,937,148 B2 | 5/2011 | Jacobson |
| 7,945,333 B2 | 5/2011 | Jacobson |
| 8,010,209 B2 | 8/2011 | Jacobson |
| 8,295,939 B2 * | 10/2012 | Jacobson ................... 607/59 |
| 2001/0031999 A1 | 10/2001 | Carter et al. |
| 2002/0032467 A1 | 3/2002 | Shemer et al. |
| 2002/0077686 A1 | 6/2002 | Westlund et al. |
| 2002/0116028 A1 | 8/2002 | Greatbatch et al. |
| 2002/0147488 A1 | 10/2002 | Doan et al. |
| 2003/0141995 A1 | 7/2003 | Lin |
| 2003/0158584 A1 | 8/2003 | Cates et al. |
| 2003/0163184 A1 | 8/2003 | Scheiner et al. |
| 2003/0199941 A1 | 10/2003 | Nielsen et al. |
| 2004/0011366 A1 | 1/2004 | Schulman et al. |
| 2004/0059392 A1 | 3/2004 | Parramon et al. |
| 2004/0116939 A1 | 6/2004 | Goode |
| 2004/0133242 A1 | 7/2004 | Chapman et al. |
| 2004/0143262 A1 | 7/2004 | Visram et al. |
| 2004/0147973 A1 | 7/2004 | Hauser |
| 2004/0167587 A1 | 8/2004 | Thompson |
| 2004/0172116 A1 | 9/2004 | Seifert et al. |
| 2004/0193223 A1 | 9/2004 | Kramer et al. |
| 2004/0249417 A1 | 12/2004 | Ransbury et al. |
| 2004/0260349 A1 | 12/2004 | Stroebel |
| 2005/0038474 A1 | 2/2005 | Wool |
| 2005/0043765 A1 | 2/2005 | Williams et al. |
| 2005/0075682 A1 | 4/2005 | Schulman et al. |
| 2005/0096702 A1 | 5/2005 | Denker et al. |
| 2005/0131478 A1 | 6/2005 | Kim et al. |
| 2005/0149138 A1 | 7/2005 | Min et al. |
| 2005/0165465 A1 | 7/2005 | Pianca et al. |
| 2005/0267555 A1 | 12/2005 | Marnfeldt et al. |
| 2005/0288722 A1 | 12/2005 | Eigler et al. |
| 2006/0064149 A1 * | 3/2006 | Belacazar et al. ............ 607/122 |
| 2006/0085039 A1 | 4/2006 | Hastings et al. |
| 2006/0085041 A1 | 4/2006 | Hastings et al. |
| 2006/0085042 A1 | 4/2006 | Hastings et al. |
| 2006/0105613 A1 | 5/2006 | Carroll |
| 2006/0108335 A1 | 5/2006 | Zhao et al. |
| 2006/0121475 A1 | 6/2006 | Davids et al. |
| 2006/0135999 A1 * | 6/2006 | Bodner et al. ................ 607/4 |
| 2006/0136004 A1 | 6/2006 | Cowan et al. |
| 2006/0161222 A1 | 7/2006 | Haubrich et al. |
| 2006/0241705 A1 | 10/2006 | Neumann et al. |
| 2006/0247750 A1 | 11/2006 | Seifert et al. |
| 2006/0282150 A1 | 12/2006 | Olson et al. |
| 2007/0016263 A1 | 1/2007 | Armstrong et al. |
| 2007/0043414 A1 | 2/2007 | Fifer et al. |
| 2007/0055184 A1 * | 3/2007 | Echt et al. ................ 601/2 |
| 2007/0088394 A1 | 4/2007 | Jacobson |
| 2007/0088396 A1 | 4/2007 | Jacobson |
| 2007/0088397 A1 | 4/2007 | Jacobson |
| 2007/0088398 A1 | 4/2007 | Jacobson |
| 2007/0123923 A1 | 5/2007 | Lindstrom et al. |
| 2007/0142709 A1 | 6/2007 | Martone et al. |
| 2007/0167994 A1 * | 7/2007 | Shelton et al. ............... 607/60 |
| 2007/0179552 A1 | 8/2007 | Dennis et al. |
| 2007/0270675 A1 | 11/2007 | Kane et al. |
| 2007/0276004 A1 | 11/2007 | Hirsch et al. |
| 2007/0276444 A1 | 11/2007 | Gelbart et al. |
| 2007/0293904 A1 | 12/2007 | Gelbart et al. |
| 2008/0004535 A1 | 1/2008 | Smits |
| 2008/0021532 A1 | 1/2008 | Kveen et al. |
| 2008/0039738 A1 | 2/2008 | Dinsmoor et al. |
| 2008/0086168 A1 | 4/2008 | Cahill |
| 2008/0091255 A1 | 4/2008 | Caparso et al. |
| 2008/0119911 A1 | 5/2008 | Rosero |
| 2008/0243218 A1 | 10/2008 | Bottomley et al. |
| 2008/0269591 A1 | 10/2008 | Halperin et al. |
| 2009/0082827 A1 | 3/2009 | Kveen et al. |
| 2009/0082828 A1 | 3/2009 | Ostroff |
| 2009/0149902 A1 | 6/2009 | Kumar et al. |
| 2009/0171408 A1 | 7/2009 | Solem |
| 2010/0069983 A1 | 3/2010 | Peacock et al. |
| 2010/0198288 A1 | 8/2010 | Ostroff |
| 2010/0249828 A1 | 9/2010 | Mavani et al. |
| 2010/0292541 A1 | 11/2010 | Hashiba et al. |
| 2010/0305653 A1 | 12/2010 | Lund et al. |
| 2010/0305656 A1 | 12/2010 | Imran et al. |
| 2010/0312332 A1 | 12/2010 | Forster et al. |
| 2011/0004117 A1 | 1/2011 | Neville et al. |
| 2011/0071586 A1 | 3/2011 | Jacobson |
| 2011/0077708 A1 | 3/2011 | Ostroff |
| 2011/0208260 A1 | 8/2011 | Jacobson |
| 2011/0218587 A1 | 9/2011 | Jacobson |
| 2011/0282423 A1 | 11/2011 | Jacobson |
| 2013/0041422 A1 | 2/2013 | Jacobson |
| 2014/0051965 A1 * | 2/2014 | Zdeblick et al. ............ 600/407 |

FOREIGN PATENT DOCUMENTS

| | | |
|---|---|---|
| JP | 05-245215 | 9/1993 |
| JP | 06/507096 | 3/2006 |
| JP | 06/516449 | 7/2006 |
| WO | WO93/12714 A1 | 7/1993 |
| WO | WO 98/37926 A1 | 9/1998 |
| WO | WO2004/012811 | 2/2004 |
| WO | WO 2006/065394 A1 | 6/2006 |
| WO | WO 2007/047681 A2 | 4/2007 |
| WO | WO 2007/059386 A2 | 5/2007 |
| WO | WO 2008/058265 A2 | 5/2008 |

OTHER PUBLICATIONS

Beeby et al.; Micromachined silicon generator for harvesting power from vibrations; (Proceedings) PowerMEMS 2004; Kyoto, Japan; pp. 104-107; Nov. 28-30, 2004.

Bordacher et al.; Impact and prevention of far-field sensing in fallback mode switches; PACE; vol. 26 (pt. II); pp. 206-209; Jan. 2003.

Brandt et al.; Far-field QRS complex sensing: prevalence and timing with bipolar atrial leads; PACE; vol. 23; pp. 315-320; Mar. 2000.

Brown, Eric S.; The atomic battery; Technology Review: Published by MIT; 4 pgs.; Jun. 16, 2005.

Irnich et al.; Do we need pacemakers resistant to magnetic resonance imaging; Europace; vol. 7; pp. 353-365; Feb. 2005.

Irnich; Electronic security systems and active implantable medical devices; Journal of PACE; vol. 25; No. 8; pp. 1235-1258; Aug. 2002.

Luechinger et al.; Force and torque effects of a 1.5-tesla MRI scanner of cardiac pacemakers and ICDs; Journal of PACE; vol. 24; No. 2; pp. 199-205; Feb. 2001.

Luechinger et al.; In vivo heating of pacemaker leads during magnetic resonance imaging; European Heart Journal; vol. 26; pp. 376-383; Feb. 2005.

Lüchinger ; Safety aspects of cardiac pacemakers in magnetic resonance imaging; Dissertation submitted to the Swiss Federal Institute of Technology Zurich; 137 pages; 2002 (month unavailable).

Nyenhuis et al.; MRI and Implanted Medical Devices: Basic Interactions with an emphasis on heating; vol. 5; No. 3; pp. 467-480; Sep. 2005.

Shellock et al.; Cardiac pacemaker: In vitro assessment at 1.5 T; Am Heart J; vol. 151; No. 2; pp. 436-443; Feb. 2006.

Khairkhahan et al.; U.S. Appl. No. 13/272,074 entitled "Delivery catheter systems and methods," filed Oct. 12, 2011.

(56) References Cited

OTHER PUBLICATIONS

Khairkhahan et al.; U.S. Appl. No. 13/272,082 entitled "Leadless cardiac pacemaker with anti-unscrewing feature," filed Oct. 12, 2011.
Ostroff, Alan; U.S. Appl. No. 13/272,092 entitled "Temperature sensor for a leadless cardiac pacemaker," filed Oct. 12, 2011.
Khairkhahan et al.; U.S. Appl. No. 13/324,781 entitled "Delivery Catheter Systems and Methods," filed Dec. 13, 2011.
Khairkhahan et al.; U.S. Appl. No. 13/324,802 entitled "Pacemaker Retrieval Systems and Methods," filed Dec. 13, 2011.
Khairkhahan et al.; U.S. Appl. No. 13/331,922 entitled "Leadless Pacemaker with Radial Fixation Mechanism," filed Dec. 20, 2011.
Jacobson, P.; U.S. Appl. No. 13/866,803 entitled "Leadless cardiac pacemaker system for usage in combination with an implantable cardioverter-defribrillator," filed Apr. 19, 2013.
Jacobson, Peter M.; U.S. Appl. No. 13/708,732 entitled "Leadless Cardiac Pacemaker Triggered by Conductive Communication," filed Dec. 7, 2012.
Varady et al.; U.S. Appl. No. 13/669,242 entitled "Leadless Cardiac Pacemaker with Integral Battery and Redundant Welds," filed Nov. 5, 2012.
Pertijs et al.; U.S. Appl. No. 13/901,414 entitled "Temperature Sensor for a Leadless Cardiac Pacemaker," filed May 23, 2013.
Ostroff et al.; U.S. Appl. No. 13/910,896 entitled "Leadless Pacemaker with Multiple Electrodes," filed Jun. 5, 2013.
Ostroff, Alan; U.S. Appl. No. 13/915,560 entitled "MRI Compatible Leadless Cardiac Pacemaker," filed Jun. 11, 2013.
Design of cardiac pacemakers, edited by J.G. Webster, 1995, chaper 11 (EP Opp).
Reply Brief, U.S. Appl. No. 12/953,282, filed Oct. 29, 2012, 4 pages.
Examiner's Answer to Appeal Brief, U.S. Appl. No. 12/953,282, mailed Aug. 30, 2012, 6 pages.
Appeal Brief, U.S. Appl. No. 12/953,282, mailed Jul. 13, 2012, 4 pages.
Final Office Action, U.S. Appl. No. 12/953,282, mailed Feb. 23, 2012, 12 pages.
Response to Office Action, U.S. Appl.No. 12/953,282, filed Dec. 22 2011, 9 pages.
Non-Final Office Aption, U.S. Appl. No. 12/953,282, mailed Jun. 7, 2011, 12 pages.
Notice of Allowance, U.S. App. No. 11/549605, mailed Feb. 22, 2011, 4 pages.
Notice of Allowance, U.S. Appl. No. 11/549605; mailed Jan. 5, 2011, 4 pages.
Non-Final Office Action, U.S. Appl. No. 11/549.605, mailed May 11, 2010, 16 pages.
Non-Final Office Action, U.S. Appl. No. 11/549.605, mailed Feb. 4, 2009, 13 pages.
Non-Final Office Action. U.S. Patent Application No. 13/109,728 mailed Jun. 25, 2012, 7 pages.
Non-Final Office Action, U.S. Application No. 13/109,728, mailed Dec. 1, 2011, 16 pages.
Appeal Brief, U.S. Appl. No. 11/549,551, filed Mar. 7, 2013 25 pages.
Final Office Action: U.S.. Patent Application No. 11/549,581. fled Oct. 16,: 2012, 28 pages.
Non-Final Office Action; U.S, Application No. 11/549.581, filed Jun. 22, 2012, 27 pages.
Notice of Allowance, U.S. Appl. No, 11/549,599, mailed Jan. 23, 2013, 7 pages.
Non-Final Office Action, U.S. Appl. No. 11/549,599, mailed Aug. 28, 2012, 12 pages.
Non-Final Office Action; U.S. Appl. No. 11/549,599, mailed May 4, 2012, 40 pages.
Final Office Action, U.S. Appl. No. 11/549599, mailed Aug. 30, 2010, 10 pages.
Non-Final Office Action, U.S. Application No, 11/549,599, mailed Mar. 17, 2010, 9 pages.
Final Office Action, U.S. Appl. No, 11/549,599, mailed Nov. 25, 2009. 14 pages.
Non-Final Office Action, U.S. Appl. No. 11/549,599. mailed Dec. 9, 2008, 35 pages.
Notice of Allowance, U.S. Appl. No, 11/549,596, mailed Sep. 10, 2012, 5 pages.
Non-Final Office Action; U.S. Appl. No. 11/549,596, mailed May 21, 2012, 8 pages.
Final Office Action, U.S. Appl. No. 11/549,596, mailed Aug. 31, 2010, 10 pages.
Non-Final Office Action, U.S. Appl. No, 11/549,596, mailed Mar. 17, 2010, 8 pages.
Final Office Action, U.S. Appl. No 1/549,596. mailed Nov. 27. 2009, 10 pages.
Non-Final Office Action, U.S. Appl. No. 11/549,596, mailed Nov. 25, 2008, 29 pages.
Reply Brief, U.S Appl. No. 111549;501, filed May 8, 2012, 4 pages.
Examiner's Answer, U.S Appl. No. 11/549,591, mailed Mar. 13, 2012. 12 pages.
Appeal Brief, U.S. Appl. No. 11/549,591, filed Oct. 10, 2011, 20 pages.
Final Office Action, U.S. Appl. No, 11/549,591, mailed Apr. 27, 2011, 11 pages.
Non-Final Office Action, U.S. Appl. No. 11/549,591, mailed Nov. 24, 2010, 10 pages.
Non-Final Office Action, U.S. Appl. No. 11/5,19591, mailed May 12, 2010, 11 pages.
Non-Final Office Action, U.S. Application No 1/549,591, mailed Dec. 9, 2008, 35 pages.
International Searching Authority, "Notification of Transmittal of the International Search Report and the Written Opinion of the International Searching Authority. Or the Declaration," International Application No. PCT/US12/57776, Jan. 10, 2013, 12 pages.
International Searching Authority, "Notification of Transmittal of the International Search Report and the Written Opinion of the International Searching Authority, or the Declaration," International Application No. PCT/US12/57776, Apr. 8, 2008 29 pages.
European Patent Office, "Communication of a Notice of Opposition," European Application No. 06836350,6, Oct. 24, 2014, 35 pages.
Decision on Appeal mailed Jun. 1, 2015; Related U.S. Appl. No. 11/549,591.

* cited by examiner

| Carrier frequency | Carrier current (patient auxiliary current) | Standards compliance path | Notes |
|---|---|---|---|
| 10kHz | <1mA | Complies with IEC-60601-1 without additional justification | May not be enough current for sufficient signal at LCP |
| 10kHz and above | < f/1e4 mA | | |
| 100kHz - 200kHz | > f/1e4 mA, <100mA/cm$^2$, <300mJ per "pulse" | Justify compliance based on:<br>• IEC-60601-1 Annex A (thermal hazard only at these frequencies)<br>• Low total energy transmitted<br>• IEC-60601-2-2 current density limit<br>• Compliance with IEC-60601-2-2 high frequency leakage requirements<br>• IEC-60601-2-10 energy limit (<300mJ per pulse into 500Ω)<br>• IEC-60601-2-10 allows current averaging over 5s to compare to 10mA limit | 60601-2-2 justifications may be weak because <200kHz. This is the frequency limit for "high frequency" as defined in that standard. |

FIGURE 12

| Carrier frequency | Carrier current (patient auxiliary current) | Standards compliance path | Notes |
|---|---|---|---|
| >200kHz | > f/1e4 mA, <100mA/cm² (-2-2) <300mJ per "pulse" (-2-10) | Justify compliance based on:<br><br>• IEC-60601-1 Annex A (thermal hazard only at these frequencies)<br><br>• Low total energy transmitted<br><br>• IEC-60601-2-2 current density limit<br><br>• Compliance with IEC-60601-2-2 high frequency leakage requirements<br><br>• IEC-60601-2-10 energy limit (<300mJ per <100ms pulse into 500Ω)<br><br>• IEC-60601-2-10 allows current averaging over 5s to compare to 10mA limit | |

FIGURE 13 ical unit circuitry within the IPG to isolate at least one conductive path between a patient's cardiac tissue and at least one contact on the electronics assembly. Suitable conductive paths exist through the housing to the patient's body tissue as well as through the electrodes. This arrangement of the feedthroughs, electronics assembly, and conductive paths provides the capability of applying pacing pulses through cardiac tissue via multiple pathways, detecting and communicating information through the housing to the patient's tissues, or conducting communication of information between multiple pacemakers in a system or with external sensors and programmers.

LEADLESS CARDIAC PACEMAKER WITH CONDUCTED COMMUNICATION

CROSS REFERENCE TO RELATED APPLICATIONS

This application is a continuation-in-part of U.S. application Ser. No. 13/109,728, entitled "PROGRAMMER FOR BIOSTIMULATOR SYSTEM", filed May 17, 2011; which is a continuation of U.S. application Ser. No. 11/549,605, entitled "PROGRAMMER FOR BIOSTIMULATOR SYSTEM," filed Oct. 13, 2006, now U.S. Pat. No. 7,945,333; which claims the benefit of priority to U.S. Provisional Application Nos. 60/726,706 entitled "LEADLESS CARDIAC PACEMAKER WITH CONDUCTED COMMUNICATION," filed Oct. 14, 2005; 60/761,531 entitled "LEADLESS CARDIAC PACEMAKER DELIVERY SYSTEM," filed Jan. 24, 2006; 60/729,671 entitled "LEADLESS CARDIAC PACEMAKER TRIGGERED BY CONDUCTED COMMUNICATION," filed Oct. 24, 2005; 60/737,296 entitled "SYSTEM OF LEADLESS CARDIAC PACEMAKERS WITH CONDUCTED COMMUNICATION," filed Nov. 16, 2005; 60/739,901 entitled "LEADLESS CARDIAC PACEMAKERS WITH CONDUCTED COMMUNICATION FOR USE WITH AN IMPLANTABLE CARDIO-VERTER-DEFIBRILLATOR," filed Nov. 26, 2005; 60/749,017 entitled "LEADLESS CARDIAC PACEMAKER WITH CONDUCTED COMMUNICATION AND RATE RESPONSIVE PACING," filed Dec. 10, 2005; and 60/761,740 entitled "PROGRAMMER FOR A SYSTEM OF LEADLESS CARDIAC PACEMAKERS WITH CONDUCTED COMMUNICATION," filed Jan. 24, 2006; all by Peter M. Jacobson, each of which are incorporated herein by reference in their entirety for all purposes.

This application is also a continuation-in-part of U.S. application Ser. No. 13/098,266, entitled "RATE RESPONSIVE LEADLESS CARDIAC PACEMAKER", filed Apr. 29, 2011; which is a continuation of U.S. patent application Ser. No. 11/549,603, entitled "RATE RESPONSIVE LEADLESS CARDIAC PACEMAKER", filed Oct. 13, 2006, now U.S. Pat. No. 7,937,148, which claims the benefit of priority to U.S. Provisional Application Nos. 60/726,706, entitled "LEADLESS CARDIAC PACEMAKER WITH CONDUCTED COMMUNICATION," filed Oct. 14, 2005; 60/761,531, entitled "LEADLESS CARDIAC PACEMAKER DELIVERY SYSTEM," filed Jan. 24, 2006; 60/729,671, entitled "LEADLESS CARDIAC PACEMAKER TRIGGERED BY CONDUCTED COMMUNICATION," filed Oct. 24, 2005; 60/737,296, entitled "SYSTEM OF LEADLESS CARDIAC PACEMAKERS WITH CONDUCTED COMMUNICATION," filed Nov. 16, 2005; 60/739,901, entitled "LEADLESS CARDIAC PACEMAKERS WITH CONDUCTED COMMUNICATION FOR USE WITH AN IMPLANTABLE CARDIOVERTER-DEFIBRILLATOR," filed Nov. 26, 2005; 60/749,017, entitled "LEADLESS CARDIAC PACEMAKER WITH CONDUCTED COMMUNICATION AND RATE RESPONSIVE PACING," filed Dec. 10, 2005; and 60/761,740, entitled "PROGRAMMER FOR A SYSTEM OF LEADLESS CARDIAC PACEMAKERS WITH CONDUCTED COMMUNICATION," filed Jan. 24, 2006; all by Peter M. Jacobson, each of which are incorporated herein by reference in their entirety for all purposes.

INCORPORATION BY REFERENCE

All publications and patent applications mentioned in this specification are herein incorporated by reference to the same extent as if each individual publication or patent application was specifically and individually indicated to be incorporated by reference.

BACKGROUND

Cardiac pacing electrically stimulates the heart when the heart's natural pacemaker and/or conduction system fails to provide synchronized atrial and ventricular contractions at appropriate rates and intervals for a patient's needs. Such bradycardia pacing provides relief from symptoms and even life support for hundreds of thousands of patients. Cardiac pacing may also give electrical overdrive stimulation intended to suppress or convert tachyarrhythmias, again supplying relief from symptoms and preventing or terminating arrhythmias that could lead to sudden cardiac death.

Cardiac pacing is usually performed by a pulse generator implanted subcutaneously or sub-muscularly in or near a patient's pectoral region. The generator usually connects to the proximal end of one or more implanted leads, the distal end of which contains one or more electrodes for positioning adjacent to the inside or outside wall of a cardiac chamber. The leads have an insulated electrical conductor or conductors for connecting the pulse generator to electrodes in the heart. Such electrode leads typically have lengths of 50 to 70 centimeters.

Known pulse generators can include various sensors for estimating metabolic demand, to enable an increase in pacing rate proportional and appropriate for the level of exercise. The function is usually known as rate-responsive pacing. For example, an accelerometer can measure body motion and indicate activity level. A pressure transducer in the heart can sense the timing between opening and closing of various cardiac valves, or can give a measure of intracardiac pressure directly, both of which change with changing stroke volume. Stroke volume increases with increased activity level. A temperature sensor can detect changes in a patient's blood temperature, which varies based on activity level. The pacemaker can increase rate proportional to a detected increase in activity.

Pulse generator parameters are usually interrogated and modified by a programming device outside the body, via a loosely-coupled transformer with one inductance within the body and another outside, or via electromagnetic radiation with one antenna within the body and another outside.

Although more than five hundred thousand pacemakers are implanted annually, various well-known difficulties are present.

The pulse generator, when located subcutaneously, presents a bulge in the skin that patients can find unsightly or unpleasant. Patients can manipulate or "twiddle" the device. Even without persistent twiddling, subcutaneous pulse generators can exhibit erosion, extrusion, infection, and disconnection, insulation damage, or conductor breakage at the wire leads. Although sub-muscular or abdominal placement can address some of concerns, such placement involves a more difficult surgical procedure for implantation and adjustment, which can prolong patient recovery.

A conventional pulse generator, whether pectoral or abdominal, has an interface for connection to and disconnection from the electrode leads that carry signals to and from the heart. Usually at least one male connector molding has at least one terminal pin at the proximal end of the electrode lead. The at least one male connector mates with at least one corresponding female connector molding and terminal block within the connector molding at the pulse generator. Usually a setscrew is threaded in at least one terminal block per electrode lead to secure the connection electrically and mechanically. One or more O-rings usually are also supplied to help maintain electrical isolation between the connector moldings. A setscrew cap or slotted cover is typically included to provide electrical insulation of the setscrew. The complex connection between connectors and leads provides multiple opportunities for malfunction.

For example, failure to introduce the lead pin completely into the terminal block can prevent proper connection between the generator and electrode.

Failure to insert a screwdriver correctly through the setscrew slot, causing damage to the slot and subsequent insulation failure.

Failure to engage the screwdriver correctly in the setscrew can cause damage to the setscrew and preventing proper connection.

Failure to tighten the setscrew adequately also can prevent proper connection between the generator and electrode, however over-tightening of the setscrew can cause damage to the setscrew, terminal block, or lead pin, and prevent disconnection if necessary for maintenance.

Fluid leakage between the lead and generator connector moldings, or at the setscrew cover, can prevent proper electrical isolation.

Insulation or conductor breakage at a mechanical stress concentration point where the lead leaves the generator can also cause failure.

Inadvertent mechanical damage to the attachment of the connector molding to the generator can result in leakage or even detachment of the molding.

Inadvertent mechanical damage to the attachment of the connector molding to the lead body, or of the terminal pin to the lead conductor, can result in leakage, an open-circuit condition, or even detachment of the terminal pin and/or molding.

The lead body can be cut inadvertently during surgery by a tool, or cut after surgery by repeated stress on a ligature used to hold the lead body in position. Repeated movement for hundreds of millions of cardiac cycles can cause lead conductor breakage or insulation damage anywhere along the lead body.

Although leads are available commercially in various lengths, in some conditions excess lead length in a patient exists and is to be managed. Usually the excess lead is coiled near the pulse generator. Repeated abrasion between the lead body and the generator due to lead coiling can result in insulation damage to the lead.

Friction of the lead against the clavicle and the first rib, known as subclavian crush, can result in damage to the lead.

In many applications, such as dual-chamber pacing, multiple leads can be implanted in the same patient and sometimes in the same vessel. Abrasion between the leads for hundreds of millions of cardiac cycles can cause insulation breakdown or even conductor failure.

Communication between the implanted pulse generator and external programmer uses a telemetry coil or antenna and associated circuitry in the pulse generator, adding complexity that increases the size and cost of devices. Moreover, power consumption from the pulse generator battery for communication typically exceeds power for pacing by one or more orders of magnitude, introducing a requirement for battery power capability that can prevent selecting the most optimal battery construction for the otherwise low-power requirements of pacing.

SUMMARY OF THE DISCLOSURE

In general, in one aspect, a leadless pacemaker for pacing a heart of a human includes a hermetic housing and at least two electrodes on or near the hermetic housing. The at least two electrodes are configured to deliver energy to stimulate the heart and to transfer information to or from at least one external device.

This and other embodiments can include one or more of the following features.

The external device can be a second leadless pacemaker, a defibrillator, a conventional pacemaker, an implanted programmer, or a programmer external to the body of the human.

The information can be encoded in sub-threshold pulses.

The leadless pacemaker can further include a pulse generator in the housing, and the pulse generator can be configured to provide energy to the at least two electrodes to stimulate the heart. The pulse generator can be further configured to provide energy to the at least two electrodes to transfer the information to the external device. The leadless pacemaker can further include a second pulse generator in the housing, and the second pulse generator can be configured to provide energy to the at least two electrodes to transfer the information signals to the external device.

The leadless pacemaker can further include a controller in the hermetic housing, and the controller can be configured to communicate with the external device by transferring the information through the at least two electrodes. The controller can be configured to communicate with the external device by transferring the information through the at least two electrodes during a pacing pulse. The controller can be configured to communicate with the external device by transferring the information through the at least two electrodes outside of a refractory period or pacing pulse. The controller can be configured to communicate with the external device by transferring the information through the at least two electrodes only during an absolute refractory period. The controller can be configured to provide charge balance of the information before the end of a refractory period. The controller can be configured to transfer information to or from the external device by sending a bell-ringer signal to the external device and listening for a response from the external device only during a set time period after the bell-ringer signal. The controller can be configured to send a synchronization signal through the at least two electrodes to the external device to start transfer of a part of the information. The controller can be configured to measure a length of time between encoded information signals received by the at least two electrodes. The controller can be further configured to use the measured length of time to estimate a clock frequency of the external device and optimize the timing of the transfer of information.

The pacemaker can be configured to discriminate signals received by the at least two electrodes for noise rejection.

In general, in one aspect, a system for pacing a heart of a human includes a leadless pacemaker and an external device not attached to the leadless pacemaker. The leadless pacemaker includes a hermetic housing and at least two electrodes on or near the hermetic housing. The at least two electrodes are configured to delivery energy to stimulate the heart and to transfer information signals to or from the external device.

This and other embodiments can include one or more of the following.

The information can include sub-threshold pulses.

The external device can be a second leadless pacemaker, a defibrillator, a conventional pacemaker, an implanted programmer, or a programmer external to the body of human.

The external device can be a programmer external to the body of the human, and the programmer can include at least two skin electrodes configured to attach to skin of the human, which are further configured to transfer information signals to or from the leadless pacemaker. The external device can further include a controller, and the controller can be configured to communicate with the leadless pacemaker by transferring the information through the at least two skin electrodes. The controller can be configured to transmit the information signals through the at least two skin electrodes using a biphasic square wave. The biphasic square have can have approximately a 25V peak amplitude.

The external device can further include a controller, and the controller can be configured to communicate with the leadless pacemaker by transferring the information signals to or from the leadless pacemaker. The controller can be configured to transfer the information signals during a pacing pulse. The controller can be configured to transfer the information signals outside of a refractory period or pacing pulse. The controller can be configured to transfer the information only during an absolute refractory period. The controller can be configured to measure a length of time between the information signals transferred from the leadless pacemaker. The controller can be further configured to use the measured length to estimate a clock frequency of the leadless pacemaker and optimize the timing of the transfer of information.

The external device can be configured to discriminate signals transferred from the leadless pacemaker for noise rejection.

In general, in one aspect, a method of pacing a heart of a human includes delivering electrical pulses through at least two electrodes of a leadless pacemaker to stimulate the heart and communication information signals between the at least two electrodes and an external device not attached to the leadless pacemaker.

This and other embodiments can include one or more of the following features.

Communicating can occur only during a refractory period. Communicating can occur outside of a refractory period or a pacing pulse. The method can further include charge balancing the information signals before the end of a refractory period. Communicating can occur only during predetermined times in one or more pacing cycles. The method can further include sending a synchronization signal through the at least two electrodes to the external device to start transfer of a part of the information signals.

BRIEF DESCRIPTION OF THE DRAWINGS

Embodiments of the invention relating to both structure and method of operation may best be understood by referring to the following description and accompanying drawings, in which similar reference characters denote similar elements throughout the several views:

FIGS. 12 and 13 are charts summarizing international standards applicable to a programmer's body electrode current.

DETAILED DESCRIPTION

Figure 1A:
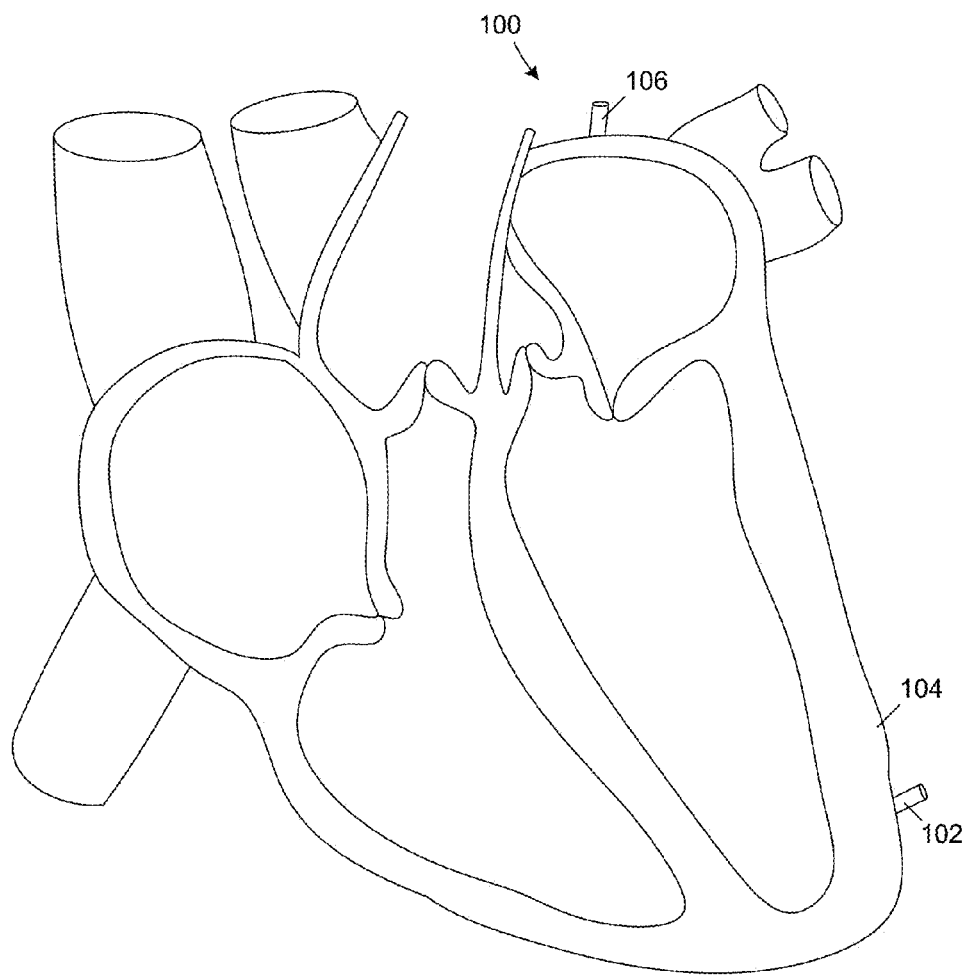
FIG. 1A is a pictorial diagram showing an embodiment of a cardiac pacing system that includes a leadless cardiac pacemaker.
Figure 1B:
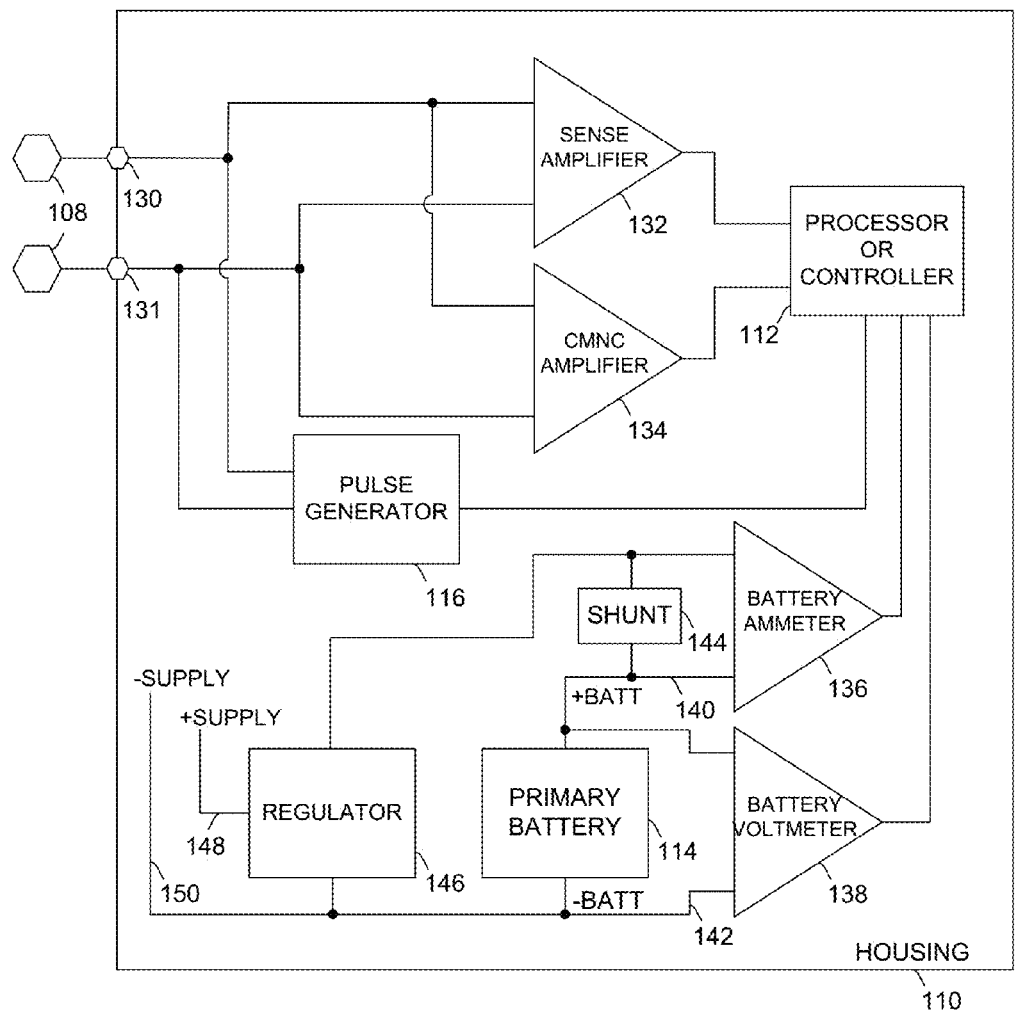
FIG. 1B is a schematic block diagram showing interconnection of operating elements of an embodiment of the illustrative leadless cardiac pacemaker.

Referring to FIGS. 1A and 1B, a pictorial view which is not shown to scale and a schematic block diagram respectively depict an embodiment of a cardiac pacing system 100 that comprises a leadless cardiac pacemaker 102. The leadless cardiac pacemaker 102 can comprise a housing 110, multiple electrodes 108 coupled to the housing 110, and a pulse delivery system hermetically contained within the housing 110 and electrically coupled to the electrodes 108. The pulse delivery system can be configured for sourcing energy internal to the housing 110, generating and delivering electrical pulses to the electrodes 108. A processor 112 can also be hermetically contained within the housing 110 as part of the pulse delivery system and is communicatively coupled to the electrodes 108. The processor 112 can control electrical pulse delivery at least partly based on the sensed activity.

In various embodiments, the electrodes 108 can be coupled on or within two centimeters of the housing 110. In some arrangements, the electrodes 108 can be formed integrally to an outer surface of the housing 110.

Referring to FIG. 1B, the leadless cardiac pacemaker 102 has functional elements substantially enclosed in a hermetic housing 110. The pacemaker has at least two electrodes 108 located within, on, or near the housing 110, for delivering pacing pulses to and sensing electrical activity from the muscle of the cardiac chamber, and for bidirectional communication with at least one other device within or outside the body. Hermetic feedthroughs 130, 131 can conduct electrode signals through the housing 110. The housing 110 contains a primary battery 114 to provide power for pacing, sensing, and communication. The housing 110 contains circuits 132 for sensing cardiac activity from the electrodes 108; circuits 134 for receiving information from at least one other device via the electrodes 108; and a pulse generator 116 for generating pacing pulses for delivery via the electrodes 108 and also for transmitting information to at least one other device via the electrodes 108. The pacemaker 102 further contains circuits for monitoring device health, for example a battery current monitor 136 and a battery voltage monitor 138. The pacemaker 102 further contains processor or controller circuits 112 for controlling these operations in a predetermined manner.

In accordance with another embodiment of a pacing system, a leadless cardiac pacemaker 102 comprises a housing 110, multiple electrodes 108 coupled to the housing 108, and a pulse generator 116 hermetically contained within the housing 110 and electrically coupled to the electrodes 108. The pulse generator 116 is configured to generate and deliver electrical pulses to the electrodes 108 powered from a source 114 contained entirely within the housing 110. An activity sensor 154 can be hermetically contained within the housing 110 and adapted to sense activity. A logic 112, for example a processor, controller, central processing unit, state machine, programmable logic array, and the like, is hermetically contained within the housing 110 and communicatively coupled to the pulse generator 116, the activity sensor 154, and the electrodes 108. In some embodiments, the logic 112 is configured to control electrical pulse delivery at least partly based on the sensed activity.

In some embodiments, the logic 112 can be a processor that controls electrical pulse delivery and/or application of the activity sensor according to one or more programmable parameters with the processor programmable by communication signals transmitted via the electrodes 108.

Also shown in FIG. 1B, the primary battery 114 has positive terminal 140 and negative terminal 142. A suitable primary battery has an energy density of at least 3 W·h/cc, a power output of 70 microwatts, a volume less than 1 cubic centimeter, and a lifetime greater than 5 years.

One suitable primary battery uses beta-voltaic technology, licensed to BetaBatt Inc. of Houston, Tex., USA, and developed under a trade name DEC™ Cell, in which a silicon wafer captures electrons emitted by a radioactive gas such as tritium. The wafer is etched in a three-dimensional surface to capture more electrons. The battery is sealed in a hermetic package which entirely contains the low-energy particles emitted by tritium, rendering the battery safe for long-term human implant from a radiological-health standpoint. Tritium has a half-life of 12.3 years so that the technology is more than adequate to meet a design goal of a lifetime exceeding 5 years.

In accordance with another embodiment of a pacing system, a leadless cardiac pacemaker 102 comprises a housing 110, multiple electrodes 108 coupled to the housing 110, and a pulse generator 116 hermetically contained within the housing 110 and electrically coupled to the electrodes 108. The pulse generator 116 generates and delivers electrical pulses to the electrodes 108, causing cardiac contractions. The pulse generator 116 also conveys information to one or more devices 106 external to the pacemaker 102, such as another pacemaker or an external programmer. The pacemaker 102 further comprises at least one amplifier 132, 134 hermetically contained within the housing 110 and electrically coupled to the electrodes 108. The amplifier or amplifiers 132, 134 are configured to amplify signals received from the electrodes 108 and to detect cardiac contractions, and further can receive information from the external device or devices 106. The pacemaker 102 further comprises a power supply 114 hermetically contained within the housing 110 and coupled to the pulse generator 116. The power supply 114 sources energy for the electrical pulses from internal to the housing 110. The pacemaker 102 has an activity sensor 154 hermetically contained within the housing 110 that senses activity. A processor 112 is hermetically contained within the housing 110 and communicatively coupled to the pulse generator 116, the amplifiers 132, 134, the activity sensor 154, and the electrodes 108. The processor 112 configured to receive amplifier output signals from the amplifier or amplifiers 132, 134 and control electrical pulse delivery at least partly based on the sensed activity.

In an illustrative embodiment, the amplifiers comprise a cardiac sensing amplifier 132 that consumes no more than 5 microwatts, a communications amplifier 134 that consumes no more than 25 microwatts, and a rate-response sensor amplifier 156 that consumes no more than 10 microwatts.

In an example embodiment, the regulator 146 can be configured to consume electrical power of no more than 2 microwatts and configured to supply electrical power of no more than 74 microwatts in the illustrative system that includes a rate-response amplifier.

The processor 112 can be configured to consume electrical power of no more than 5 microwatts averaged over one cardiac cycle.

Current from the positive terminal 140 of primary battery 114 flows through a shunt 144 to a regulator circuit 146 to create a positive voltage supply 148 suitable for powering the remaining circuitry of the pacemaker 102. The shunt 144 enables the battery current monitor 136 to provide the processor 112 with an indication of battery current drain and indirectly of device health.

The illustrative power supply can be a primary battery 114 such as a beta-voltaic converter that obtains electrical energy from radioactivity. In some embodiments, the power supply can be selected as a primary battery 114 that has a volume less than approximately 1 cubic centimeter.

In an illustrative embodiment, the primary battery 114 can be selected to source no more than 75-80 microwatts instantaneously since a higher consumption may cause the voltage across the battery terminals to collapse. Accordingly in one illustrative embodiment the circuits depicted in FIG. 1B can be designed to consume no more than a total of 74 microwatts. The design avoids usage of a large filtering capacitor for the power supply or other accumulators such as a supercapacitor or rechargeable secondary cell to supply peak power exceeding the maximum instantaneous power capability of the battery, components that would add volume and cost.

In various embodiments, the system can manage power consumption to draw limited power from the battery, thereby reducing device volume. Each circuit in the system can be designed to avoid large peak currents. For example, cardiac pacing can be achieved by discharging a tank capacitor (not shown) across the pacing electrodes. Recharging of the tank capacitor is typically controlled by a charge pump circuit. In a particular embodiment, the charge pump circuit is throttled to recharge the tank capacitor at constant power from the battery.

In various embodiments, the activity sensor 154 is adapted for controlling rate-responsive pacing and may use any appropriate technology, for the example the activity sensor 154 may be an accelerometer, a temperature sensor, a pressure sensor, or any other suitable sensor. In an illustrative embodiment, the activity sensor 154 can operate with a power requirement of no more than 10 microwatts.

FIG. 1B shows a pacemaker embodiment wherein the activity sensor comprises an accelerometer 154 and an accelerometer amplifier 156 configured to detect patient activity for rate-responsive pacing. The accelerometer amplifier output terminal is connected to the processor 112. Because the leadless cardiac pacemaker 102 is attached to cardiac muscle 104, the accelerometer 154 measures some acceleration due to heartbeats in addition to the desired activity signal. Processor 112 performs sampling of the accelerometer output signal synchronously with the cardiac cycle as determined by the cardiac sensing amplifier 132 and the pulse generator 116.

Processor 112 then compares acceleration signals taken at the same relative time in multiple cardiac cycles to distinguish the part of the acceleration signal that results from activity and is not due to heart wall motion.

In other embodiments, the accelerometer 154 and accelerometer amplifier 156 shown in FIG. 1B can be replaced with a temperature transducer such as a thermistor and a signal conditioning amplifier connected to processor 112. In another embodiment, a pressure transducer and signal conditioning amplifier can be connected to processor 112. Temperature is not sensitive to the cardiac cycle so that in such an activity sensor rate-responsive cardiac pacemaker embodiments, synchronous sampling with the cardiac cycle is superfluous. Although pressure varies in the cardiac cycle, easily measured features of the pressure wave, for example peak amplitude, peak-to-peak amplitude, peak rate of change (delta), and the like, can indicate the level of activity.

Figure 2:
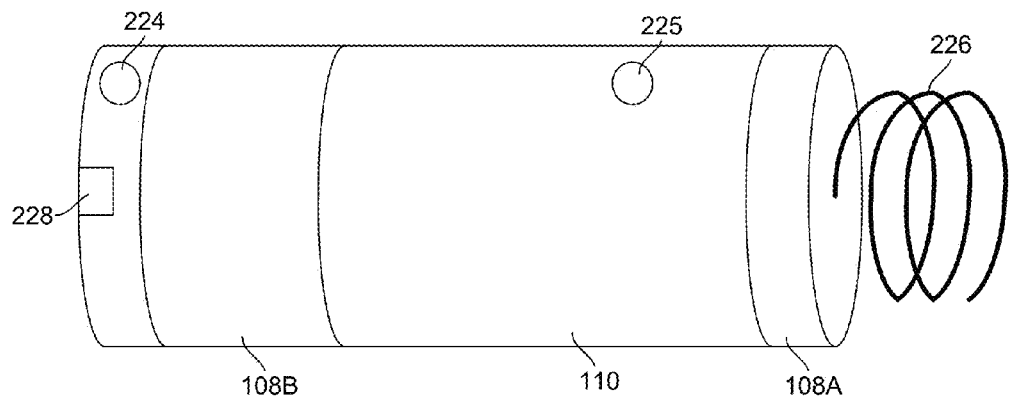
FIG. 2 is a pictorial diagrams showing the physical location of some elements of an embodiment of a leadless cardiac pacemaker.

Also shown in FIG. 2, a cylindrical hermetic housing 110 is shown with annular electrodes 108 at housing extremities. In one embodiment, the housing 110 can be composed of alumina ceramic which provides insulation between the electrodes. The electrodes 108 are deposited on the ceramic, and are platinum or platinum-iridium.

Several techniques and structures can be used for attaching the housing 110 to the interior or exterior wall of cardiac muscle 104.

A helix 226 and slot 228 enable insertion of the device endocardially or epicardially through a guiding catheter. A screwdriver stylet can be used to rotate the housing 110 and force the helix 226 into muscle 104, thus affixing the electrode 108A in contact with stimulable tissue. Electrode 108B can serve as an indifferent electrode for sensing and pacing. The helix 226 may be coated for electrical insulation, and a steroid-eluting matrix may be included near the helix to minimize fibrotic reaction, as is known in conventional pacing electrode-leads.

In other configurations, suture holes 224 and 225 can be used to affix the device directly to cardiac muscle with ligatures, during procedures where the exterior surface of the heart can be accessed.

Other attachment structures used with conventional cardiac electrode-leads including tines or barbs for grasping trabeculae in the interior of the ventricle, atrium, or coronary sinus may also be used in conjunction with or instead of the illustrative attachment structures.

Figure 3:
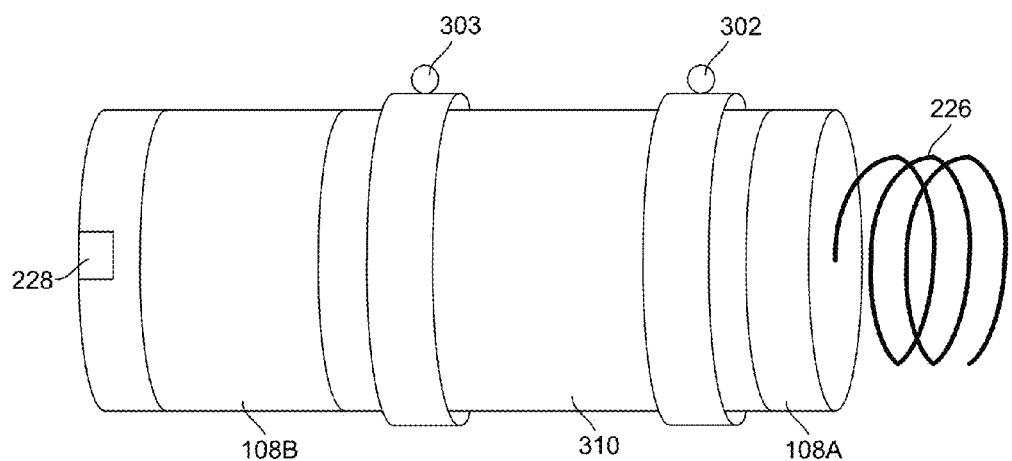
FIG. 3 is a pictorial diagram that depicts the physical location of some elements in an alternative embodiment of a leadless cardiac pacemaker.

Referring to FIG. 3, a pictorial view shows another embodiment of a pulse generator that includes a cylindrical metal housing 310 with an annular electrode 108A and a second electrode 108B. Housing 310 can be constructed from titanium or stainless steel. Electrode 108A can be constructed using a platinum or platinum-iridium wire and a ceramic or glass feed-thru to provide electrical isolation from the metal housing. The housing can be coated with a biocompatible polymer such as medical grade silicone or polyurethane except for the region outlined by electrode 108B. The distance between electrodes 108A and 108B should be selected to optimize sensing amplitudes and pacing thresholds. A helix 226 and slot 228 can be used for insertion of the device endocardially or epicardially through a guiding catheter. In addition, suture sleeves 302 and 303 made from silicone can be used to affix to the device directly to cardiac muscle with ligatures.

In accordance with another embodiment of a pacing system 100, a pacemaker configured as a leadless cardiac pacemaker 102 comprising a housing 110, and multiple electrodes 108 coupled to the housing 110. A pulse generator 116 hermetically contained within the housing 110 and electrically coupled to the electrodes 108 and is configured for generating and delivering electrical pulses to the electrodes 108. In some embodiments, an activity sensor 154 can be is hermetically contained within the housing 110 and adapted to sense activity. A processor 112 is hermetically contained within the housing and communicatively coupled to the pulse generator 116, the activity sensor 154, and/or the electrodes 108. The processor 112 controls electrical pulse delivery, for example at least partly based on the sensed activity, and communicates with one or more devices 106 external to the pacemaker 102 via signals conducted through the same electrodes 108.

Communication Generally

The leadless cardiac pacemaker or pacemakers described herein can be configured to detect a natural cardiac depolarization, time a selected delay interval, and deliver an information-encoded pulse to another pacemaker or to an external programmer. Information can be transmitted through the communication channel with no separate antenna or telemetry coil. Communication bandwidth is low with only a small number of bits encoded on each pulse.

The information communicated on the incoming communication channel can include, but is not limited to pacing rate, pulse duration, sensing threshold, and other parameters commonly programmed externally in typical pacemakers. The information communicated on the outgoing communication channel can include, but is not limited to programmable parameter settings, event counts (pacing and sensing), battery voltage, battery current, and other information commonly displayed by external programmers used with common pacemakers. The outgoing communication channel can also echo information from the incoming channel, to confirm correct programming.

In some embodiments, information is encoded, for example, as a binary code in one or more notches interrupting a stimulation pulse. Information can otherwise or also be encoded in selected or designated codes as variations in pacing pulse width of a stimulation pulse. Information can also be conveyed as electrical energy in a stimulation pulse in designated codes encoding the information in modulation of off-time between pacing pulses.

In some embodiments, information can be encoded using a technique of gating the pacing pulse for very short periods of time at specific points in the pacing pulse. During the gated sections of the pulse, no current flows through the electrodes of a leadless cardiac pacemaker. Timing of the gated sections can be used to encode information. The specific length of a gated segment depends on the programmer's ability to detect the gated section. A certain amount of smoothing or low-pass filtering of the signal can be expected from capacitance inherent in the electrode/skin interface of the programmer as well as the electrode/tissue interface of the leadless cardiac pacemaker. A gated segment is set sufficiently long in duration to enable accurate detection by the programmer, limiting the amount of information that can be transmitted during a single pacing pulse. Accordingly, a technique for communication can comprise generating stimulation pulses on stimulating electrodes of an implanted pacemaker and encoding information onto generated stimulation pulses. Encoding information onto the pulses can comprise gating the stimulation pulses for selected durations at selected timed sections in the stimulation pulses whereby gating removes current flow through the stimulating electrodes and timing of the gated sections encodes the information.

Another method of encoding information on pacing pulses involves varying the timing between consecutive pacing pulses in a pulse sequence. Pacing pulses, unless inhibited or triggered, occur at predetermined intervals. The interval between any two pulses can be varied slightly to impart information on the pulse series. The amount of information, in bits, is determined by the time resolution of the pulse shift. The steps of pulse shifting are generally on the order of microseconds. Shifting pulses by up to several milliseconds does not have an effect on the pacing therapy and cannot be sensed by the patient, yet significant information can be transmitted by varying pulse intervals within the microsecond range. The method of encoding information in variation of pulses is less effective if many of the pulses are inhibited or triggered. Accordingly, a technique for communication can comprise generating stimulation pulses on stimulating electrodes of an implanted pacemaker and encoding information onto generated stimulation pulses comprising selectively varying timing between consecutive stimulation pulses.

Alternatively or in addition to encoding information in gated sections and/or pulse interval, overall pacing pulse width can be used to encode information.

The described methods of encoding information on pacing pulses can use the programmer to distinguish pacing pulses from the patient's normal electrocardiogram, for example by recognition of the specific morphology of the pacing pulse compared to the R-wave generated during the cardiac cycle. For example, the external programmer can be adapted to distinguish a generated cardiac pacing pulse from a natural cardiac depolarization in an electrocardiogram by performing comparative pattern recognition of a pacing pulse an an R-wave produced during a cardiac cycle.

In various embodiments, the pacemaker can transmit and/or receive information such as programmable parameter settings, event counts, power-supply voltage, power-supply current, and rate-response control parameters adapted for converting an activity sensor signal to a rate-responsive pacing parameter.

Information can be transferred between the leadless pacemaker and an external device at various points during the pacing cycle (i.e. the time between heartbeats). For example, the processor 112 of the pacemaker (See, FIG. 2) can be configured to deliver the information during a pacing pulse, during a refractory period, and/or outside of the pacing pulse and the refractory period.

To transfer information outside of both the pacing pulse and the refractory period, the pulse or pulses that transfer the information are configured so as not to stimulate the heart or induce an arrhythmia. To prevent stimulation or arrhythmia induction, the transmitted pulses used to communicate information have a combination of pulse repetition rate, pulse count, and pulse amplitude that keep the transmitted pulses below the stimulation threshold. Further, the transmitted pulses are configured on as to not interfere with the pacemaker's ability to sense natural heartbeats. To avoid such interference, the transmitted pulse or pulses transmitted pulse or pulses used to communicate information can have a combination of pulse duration, pulse repetition rate, pulse count, and pulse amplitude that keeps the pulses below the pacemaker's detection threshold. Alternatively, the pacemaker's sensing amplifier input can be "blanked" or prohibited from sensing. This blanking can be accomplished by disconnecting the sensing amplifier from the electrodes during the transmission of communication pulses, blocking the sensing amplifier's output, or reducing the sensing amplifier's gain.

Figure 4:
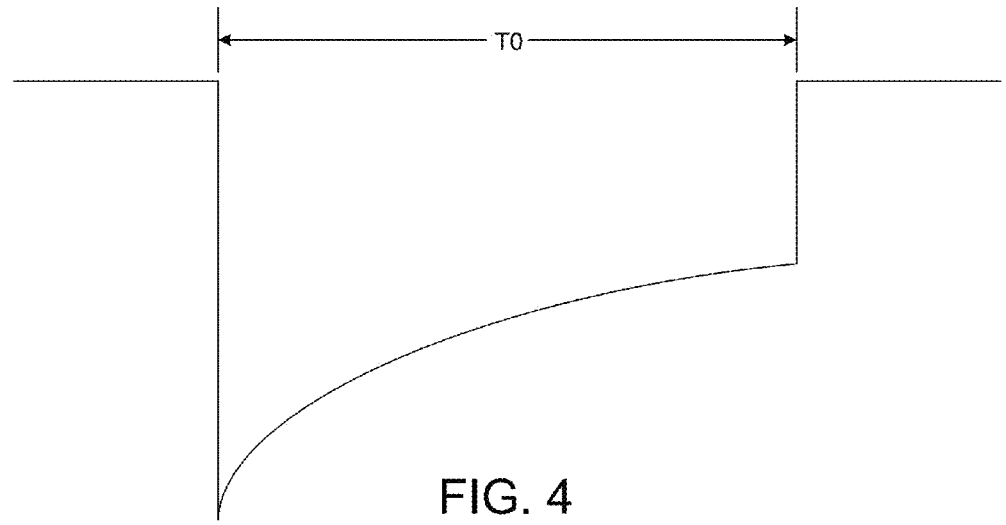
FIG. 4 is a time waveform graph illustrating a conventional pacing pulse.

Referring to FIG. 4, a typical output-pulse waveform for a conventional pacemaker is shown. The approximately-exponential decay is due to discharge of a capacitor in the pacemaker through the approximately-resistive load presented by the electrodes/tissue interface and leads. Typically the generator output is capacitor-coupled to one electrode to ensure net charge balance. The pulse duration is shown as T0 and is typically 500 microseconds.

When a pacemaker is supplying a pacing pulse but is not sending data for communication, the waveform can resemble that shown in FIG. 4.

In some embodiments, configurations, or conditions, the pacemaker is configured to generate and deliver electrical energy with the stimulation pulse interrupted by at least one notch that conveys information to a device external to the pacemaker.

Figure 5:
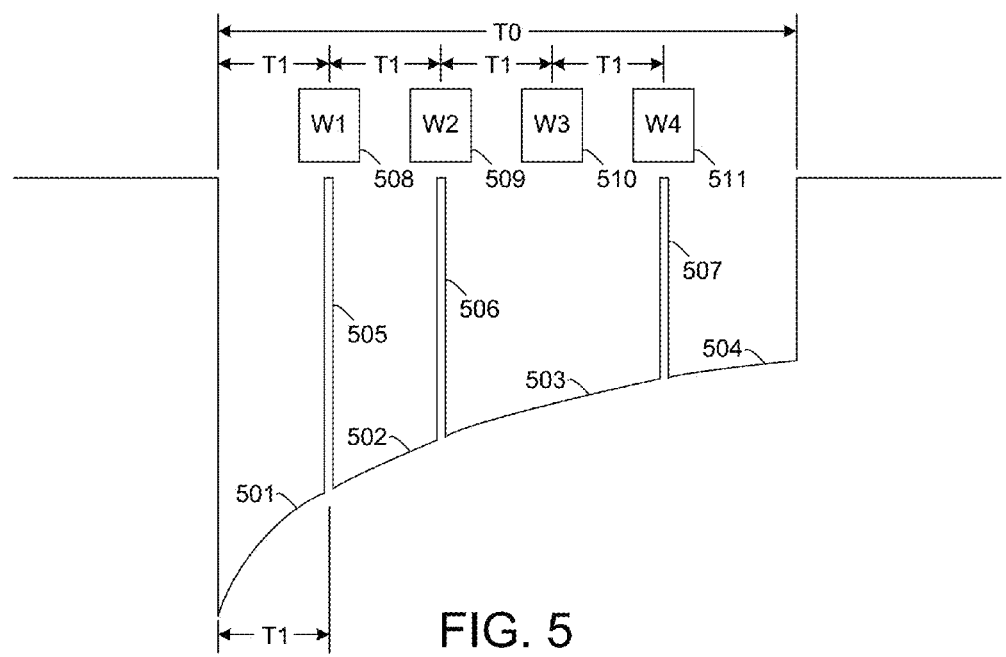
FIG. 5 is a time waveform graph depicting a pacing pulse adapted for communication as implemented for an embodiment of the illustrative pacing system.

Referring to FIG. 5, a time waveform graph depicts an embodiment of a sample output-pacing pulse waveform adapted for communication. The output-pulse waveform of the illustrative leadless pacemaker is shown during a time when the pacemaker is sending data for communication and also delivering a pacing pulse, using the same pulse generator and electrodes for both functions.

FIG. 5 shows that a pulse generator of a pacemaker has divided the output pulse into shorter pulses 501, 502, 503, 504; separated by notches 505, 506, and 507. The pulse generator times the notches 505, 506, and 507 to fall in timing windows W1, W2, and W4 designated 508, 509, and 511 respectively. Note that the pacemaker does not form a notch in timing window W3 designated 510. The timing windows are each shown separated by a time T1, approximately 100 microseconds in the example.

As controlled by the pacemaker's processor, the pulse generator selectively generates or does not generate a notch in each timing window 508, 509, 510, and 511 so that the pacemaker encodes four bits of information in the pacing pulse. A similar scheme with more timing windows can send more or fewer bits per pacing pulse. The width of the notches is small, for example approximately 15 microseconds, so that the delivered charge and overall pulse width, specifically the sum of the widths of the shorter pulses, in the pacing pulse is substantially unchanged from that shown in FIG. 4. Accordingly, the pulse shown in FIG. 5 can have approximately the same pacing effectiveness as that shown in FIG. 4, according to the law of Lapique which is well known in the art of electrical stimulation.

In a leadless cardiac pacemaker, a technique can be used to conserve power when detecting information carried on pacing pulses from other implanted devices. The leadless cardiac pacemaker can have a receiving amplifier that implements multiple gain settings and uses a low-gain setting for normal operation. The low-gain setting could be insufficiently sensitive to decode gated information on a pacing pulse accurately but could detect whether the pacing pulse is present. If an edge of a pacing pulse is detected during low-gain operation, the amplifier can be switched quickly to the high-gain setting, enabling the detailed encoded data to be detected and decoded accurately. Once the pacing pulse has ended, the receiving amplifier can be set back to the low-gain setting. For usage in the decoding operation, the receiving amplifier is configured to shift to the more accurate high-gain setting quickly when activated. Encoded data can be placed at the end of the pacing pulse to allow a maximum amount of time to invoke the high-gain setting.

In some embodiments, configurations, or conditions, a leadless pacemaker configured to generate and deliver electrical energy with the stimulation pulse that conveys information to a device external to the pacemaker in designated codes encoding the information in modulation of off-time between pacing pulses.

Figure 6:
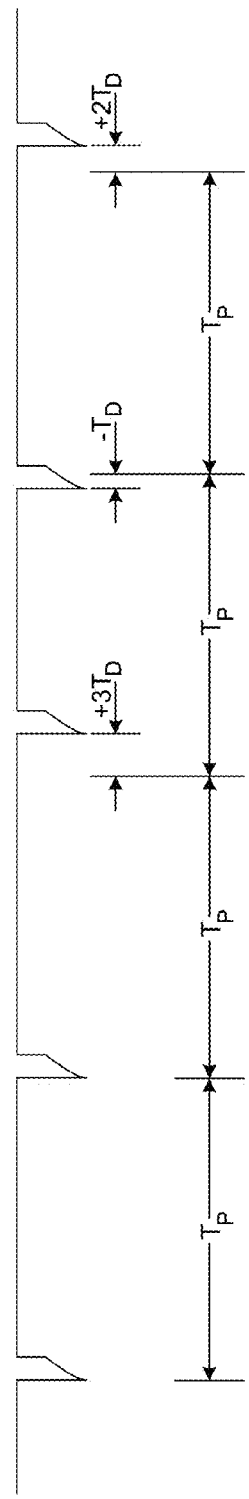
FIG. 6 is a time waveform graph showing a sample pulse waveform using off-time variation for communication.

As an alternative or in addition to using notches in the stimulation pulse, the pulses can be generated with varying off-times, specifically times between pulses during which no stimulation occurs. The variation of off-times can be small, for example less than 10 milliseconds total, and can impart information based on the difference between a specific pulse's off-time and a preprogrammed off-time based on desired heart rate. For example, the device can impart four bits of information with each pulse by defining 16 off-times centered around the preprogrammed off-time. FIG. 6 is a graph showing a sample pulse generator output which incorporates a varying off-time scheme. In the figure, time $T_p$ represents the preprogrammed pulse timing. Time $T_d$ is the delta time associated with a single bit resolution for the data sent by the pulse generator. The number of $T_d$ time increments before or after the moment specified by $T_p$ gives the specific data element transmitted. The receiver of the pulse generator's communication has advance information of the time $T_p$. The communication scheme is primarily applicable to overdrive pacing in which time $T_p$ is not changing based on detected beats.

In some embodiments, configurations, or conditions, the pacemaker is configured to generate and deliver electrical energy with the stimulation pulse that conveys information to a device external to the pacemaker in designated codes encoding the information in pacing pulse width.

FIG. 5 depicts a technique in which information is encoded in notches in the pacing pulse. FIG. 6 shows a technique of conveying information by modulating the off-time between pacing pulses. Alternatively or in addition to the two illustrative coding schemes, overall pacing pulse width can be used to impart information. For example, a paced atrial beat may exhibit a pulse width of 500 microseconds and an intrinsic atrial contraction can be identified by reducing the pulse width by 30 microseconds. Information can be encoded by the absolute pacing pulse width or relative shift in pulse width. Variations in pacing pulse width can be relatively small and have no impact on pacing effectiveness.

To ensure the leadless cardiac pacemaker functions correctly, a specific minimum internal supply voltage is maintained. When pacing tank capacitor charging occurs, the supply voltage can drop from a pre-charging level which can become more significant when the battery nears an end-of-life condition and has reduced current sourcing capability. Therefore, a leadless cardiac pacemaker can be constructed with a capability to stop charging the pacing tank capacitor when the supply voltage drops below a specified level. When charging ceases, the supply voltage returns to the value prior to the beginning of tank capacitor charging.

The illustrative scheme for transmitting data does not significantly increase the current consumption of the pacemaker. For example, the pacemaker could transmit data continuously in a loop, with no consumption penalty.

The illustrative example avoids usage of radiofrequency (RF) communication to send pacing instructions to remote electrodes on a beat-to-beat basis to cause the remote electrodes to emit a pacing pulse. RF communication involves use of an antenna and modulation/demodulation unit in the remote electrode, which increase implant size significantly. Also, communication of pacing instructions on a beat-to-beat basis increases power requirements for the main body and the remote electrode. In contrast, the illustrative system and stimulator do not require beat-to-beat communication with any controlling main body.

Exemplary Embodiment—External Programmer

In some embodiments, the device that a leadless pacemaker communicates with can be another leadless pacemaker, a conventional leaded pacemaker, a defibrillator, an implanted programmer, or an external programmer.

Figure 7A:
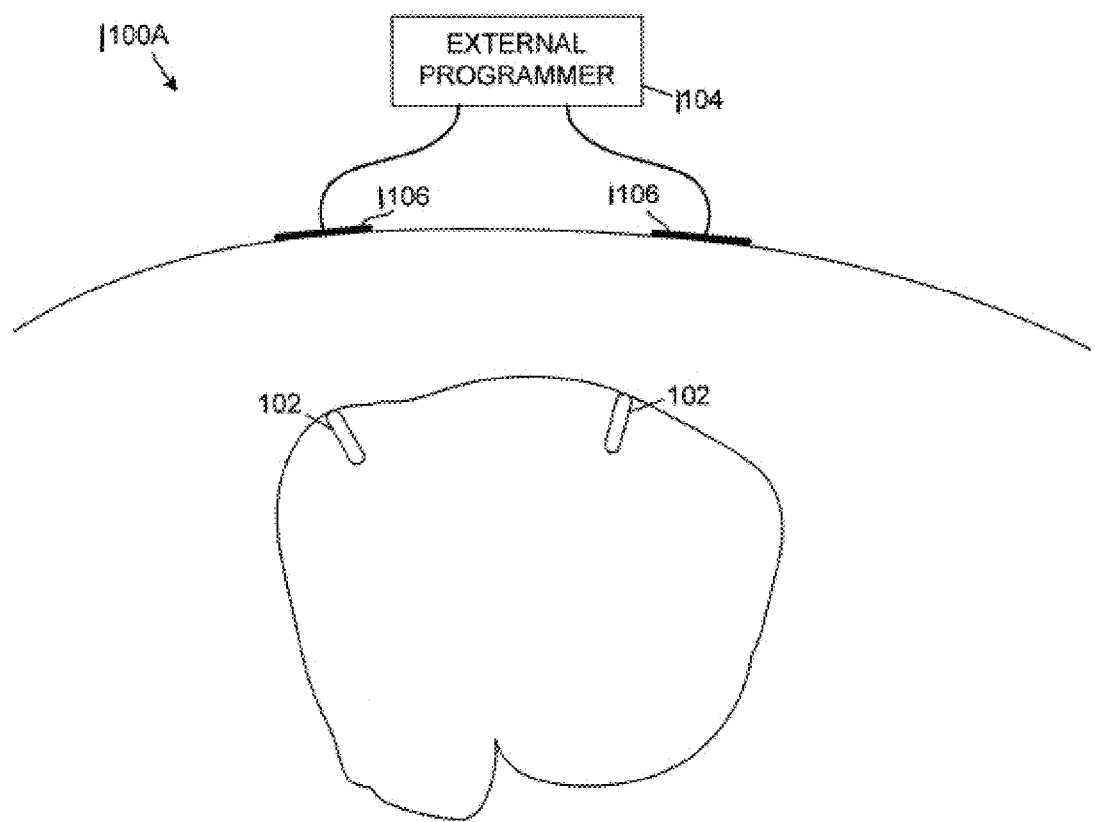
FIGS. 7A and 7B are pictorial diagrams showing embodiments of pacemaker systems including two leadless cardiac pacemakers secured to internal and to external surfaces of the heart, respectively, and an external programmer and two surface electrodes.
Figure 7B:
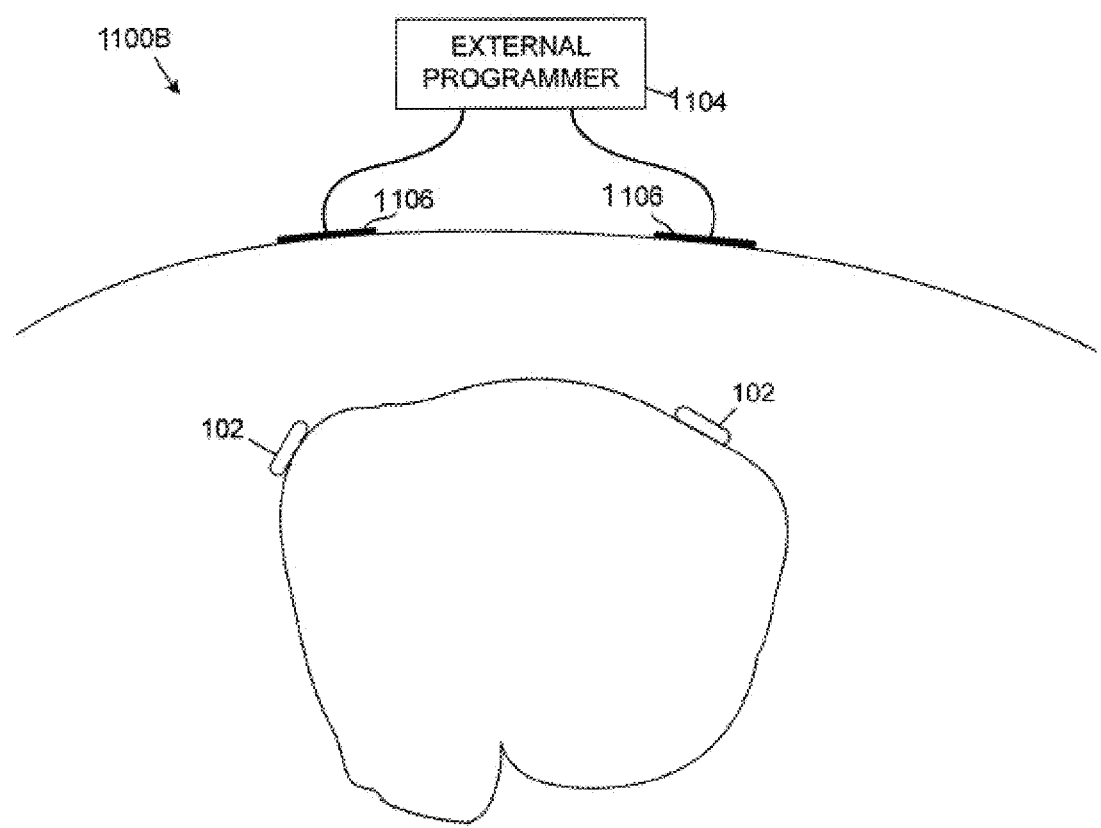

FIGS. 7A and 7B show a pacemaker system in which the device 106 is an external programmer 1104. The pacemaker systems 1100A, 1100B comprise one or more implantable devices 102 and an external programmer 1104 configured for communicating with the one or more implantable devices 102 via bidirectional communication pathways comprising a receiving pathway that decodes information encoded on stimulation pulses generated by one or more of the implantable devices 102 and conducted through body tissue to the external programmer 1104.

According to the illustrative arrangement, the bidirectional communication pathways can be configured for communication with multiple leadless cardiac pacemakers 102 via two or more electrodes 1106 and conduction through body tissue.

In accordance with various pacemaker system embodiments, an external device or module 1104 is connected by a communication transmission channel and has transmitting and receiving functional elements for a bidirectional exchange of information with one or more implanted medical devices 102. The communication channel includes two or more electrodes 1106 which can be affixed or secured to the surface of the skin. From the point of the skin, the communication transmission channel is wireless, includes the ion medium of the infra- and extra-cellular body liquids, and enables electrolytic-galvanic coupling between the surface electrodes and the implantable modules 1104.

In the pacemaker systems 1100A, 1100B, the bidirectional communication pathways can further comprise a transmitting pathway that passes information from the external programmer 1104 to one or more of the implantable devices 102 by direct conduction through the body tissue by modulation that avoids skeletal muscle stimulation using modulated signals at a frequency in a range from approximately 10 kHz to 500 kHz, for example 100 kHz to 300 kHz, such as approximately 250 kHz.

Information transmitted from the external programmer 1104 to the implanted devices 102 is conveyed by modulated signals at the approximate range of 10 kHz to 100 kHz which is a medium-high frequency. The signals are passed through the communication transmission channel by direct conduction. A modulated signal in the frequency range has a sufficiently high frequency to avoid any depolarization within the living body which would lead to activation of the skeletal muscles and discomfort to the patient. The frequency is also low enough to avoid causing problems with radiation, crosstalk, and excessive attenuation by body tissue. Thus, information may be communicated at any time, without regard to the heart cycle or other bodily processes. No restriction is imposed regarding location of electrode placement on the body because low signal attenuation enables the signal to travel throughout the body and to be received by the implanted devices 102.

In some embodiments, the bidirectional communication pathways can further comprise a receiving pathway including a low-pass filter adapted to separate the electrocardiogram from the information signals. The same surface electrodes 1106 that are used to transmit the information through the communication channel may also be used to detect a patient's electrocardiogram. Electrocardiogram frequencies are generally between 1 and 100 Hz, far lower than the 10 kHz to 100 kHz range of frequencies used to transmit information through the communication transmission channel. Therefore, the electrocardiogram can be separated from the information signal by a low-pass filter and can optionally be displayed by the programmer 1104. In addition to low-pass filtering, blanking techniques that are typical in processing of cardiac signals can be used when the communication channel is active to prevent noise or erroneous signals from the communication channel affecting the electrocardiogram channel.

Because a plurality of implantable devices 102 can be present, communication of information from the programmer is detected by all devices, enabling information to be sent to each implanted device without sending the same information multiple times.

In various embodiments and applications, the bidirectional communication pathways can further comprise a transmitting pathway that passes information from the programmer 1104 to the one or more implantable devices 102 in a common communication event whereby information is sent to one or more target devices of the implantable devices 102 using a selected technique. For example, information specific to a single implantable device or a subset of implantable devices having a unique address can be assigned to the single implantable device or the subset of implantable devices and encoded in the information. In another technique, information can designate a specific function that is executed by a particular implantable device or a particular subset of implantable devices. The information is passed to one or more implantable devices without sending individual address information for activating execution by the particular implantable device or the particular subset of implantable devices alone. In another technique, information can designate a specific function that is executed by a particular implantable device or a particular subset of implantable devices that have programming specific to the function adapted to recognize the received information is relevant to the function.

Specifically, information that is specific to a single implanted device or a subset of devices can be sent. A unique address can be assigned to each device or subset. The address can be encoded in the information sent to the plurality of devices, and any individual device can make use only of information that matches either the address or the address of the subset to which the particular device belongs.

In another technique, if each implanted device 102 or subset of devices 102 serves a specific function, which is different from other implanted devices, then information may be passed to the specific device or subset without the additional overhead of a group or individual address. For example, the device or subset can be responsible for only a specific function. When the programmer transmits information to the entire group, but the information is relevant to only the device or subset of that group, then any devices that cannot make use of the information may ignore the information. Each device has unique programming specific to a particular function and can recognize whether received information is relevant to the function. Devices operative in conjunction with the technique can be non-generic and perform specific functions, or can be generic devices with general functionality that can be made more specific by programming. Accordingly, functionality of a device can be defined at manufacture or may be defined at implantation or thereafter. The function of each device can be defined at the time of manufacture and the devices labeled or marked such that the associated function can be known upon inspection.

In some embodiments, the one or more implantable devices 102 can comprise one or more leadless cardiac pacemakers that generate cardiac pacing pulses and encode information onto the generated cardiac pacing pulses by selective alteration of pacing pulse morphology that is benign to therapeutic effect and energy cost of the pacing pulse. The cardiac pacing pulses conduct into body tissue via the electrodes for antenna-less and telemetry coil-less communication. For information transmitted from the implanted leadless cardiac pacemaker 102 to the external programmer 1104, a communication scheme can be used in which the information is encoded on the pacing pulse. The pulse morphology is altered to contain the encoded information without altering the therapeutic benefits of the pacing pulse. The energy delivered by the pacing pulse remains essentially the same after the information is encoded. The external programmer 1104 receives the pacing pulses through the associated surface electrodes 1106. Encoded information is drawn from the pacing pulses and can contain state information of the implantable leadless cardiac pacemaker, such as battery voltage, lead impedance, sensed electrocardiogram amplitude, pacemaker current drain, programmed parameters, or other parameters.

The illustrative external programmer 1104 and associated operating methods or techniques enable presentation to the user of information gathered from the implanted pacemaker or leadless cardiac pacemakers 102 using conductive communication. Some of the information to be presented may include battery voltage, lead impedance, electrocardiogram amplitude, or current drain of the device. The information can be presented in addition to other information such as parameters to be set and programmed into the leadless cardiac pacemaker. The information can be presented to a user on a display screen. Some embodiments or configurations of an external programmer 1104 can include a secondary link, for example either wireless or through a cable, to another display device, such as a handheld computer or terminal. The secondary link can also include communication over a local area network or the interact for display at a remote terminal.

FIG. 7A depicts a sample configuration involving the external programmer 1104 and two endocardially implanted leadless cardiac pacemakers 102. The external programmer 1104 is physically connected to the skin surface via two electrodes 1106, which serve three functions. First, the electrodes 1106 transmit encoded information from the programmer 1104 to the implanted leadless cardiac pacemakers 102 using a modulated signal at a medium frequency 10 kHz to 100 kHz. Second, the electrodes 1106 receive information from individual leadless cardiac pacemakers 102 by detecting encoded information in the pacing pulses of the leadless cardiac pacemakers 102. Third, the electrodes 1106 receive surface electrocardiogram for display and analysis by the programmer 1104.

In FIG. 7A, the two leadless cardiac pacemakers 102 are implanted endocardially. Thus, in a pacemaker system 1100A or 1100B an implantable device 102 may comprise one or more leadless cardiac pacemakers that can be implanted adjacent to an inside or an outside wall of a cardiac chamber. Referring to FIG. 7B, a similar system is represented with a difference that the two leadless cardiac pacemakers 102 are implanted by affixing to the exterior surface of the heart. The electrodes 1106 and programmer 1104 function similarly in arrangements shown in FIGS. 7A and 7B whether the leadless cardiac pacemakers 102 are implanted endocardially or epicardially (on the external heart surface). No restriction is imposed that the leadless cardiac pacemakers are all implanted inside or all implanted outside the heart. One or more may be implanted endocardially along with others implanted on the outer surface of the heart. The functioning of the programmer 1104 is substantially. the same. Although two electrodes 1106 are shown in FIGS. 7A and 7B, two is generally the minimum number for adequate conductive communication. More electrodes can be used, enabling an electrocardiogram (ECG) to be sensed at multiple vectors for better analysis. More than two electrodes also enable a choice of vectors for conducted communication with the leadless cardiac pacemakers, thereby maximizing the signal to noise ratio of the system. FIGS. 7A and 7B each depict two leadless cardiac pacemakers 102. One, two, or more leadless cardiac pacemakers can be implanted, depending on the number of pacemakers appropriate for effective therapy.

In various embodiments, the external programmer 1104 can be configured to perform one or more operations such as electrocardiogram sensing, retrieving status information from implanted pacemakers, modifying configuration parameters of multiple implanted pacemakers simultaneously in information passed through a common electrode set, displaying electrocardiograms, displaying information received from the at least one implantable device, and others.

In various embodiments, a pacemaker 102 can manage power consumption to draw limited power from an internal battery, thereby reducing device volume. Each circuit in the pacemaker can be designed to avoid large peak currents. For example, cardiac pacing can be achieved by discharging a tank capacitor (not shown) across the pacing electrodes. Recharging of the tank capacitor is typically controlled by a charge pump circuit. In a particular embodiment, the charge pump circuit can be throttled to recharge the tank capacitor at constant power from the battery. The one or more leadless cardiac pacemakers can be configured to charge the tank capacitor in preparation for stimulation pulse generation, time one or more windows between pulse generation, disable charging of the tank capacitor during the one or more timed windows, and enable a receive amplifier in the implanted pacemaker while the tank capacitor is disabled.

In some embodiments, the external programmer 1104 can detect a stimulation pulse from a leadless cardiac pacemaker 102 and transmit data after a selected delay to coincide with a window in which the leadless cardiac pacemaker's receiving amplifier is enabled.

The implantable devices 102 can encode and/or decode information using various techniques such as encoding the information using pacing pulse width, binary-coded notches in a pacing pulse, modulation of off-time between pacing pulses, or other suitable encoding techniques. The external programmer 1104 can encode and/or decode information using on-off keying encoding and modulation techniques depicted in FIG. 9. However, any other appropriate method can be used whereby a modulated bit-stream can be generated at a medium high frequency, for example frequency-shift keying, frequency modulation, or amplitude shift keying.

Figure 8:
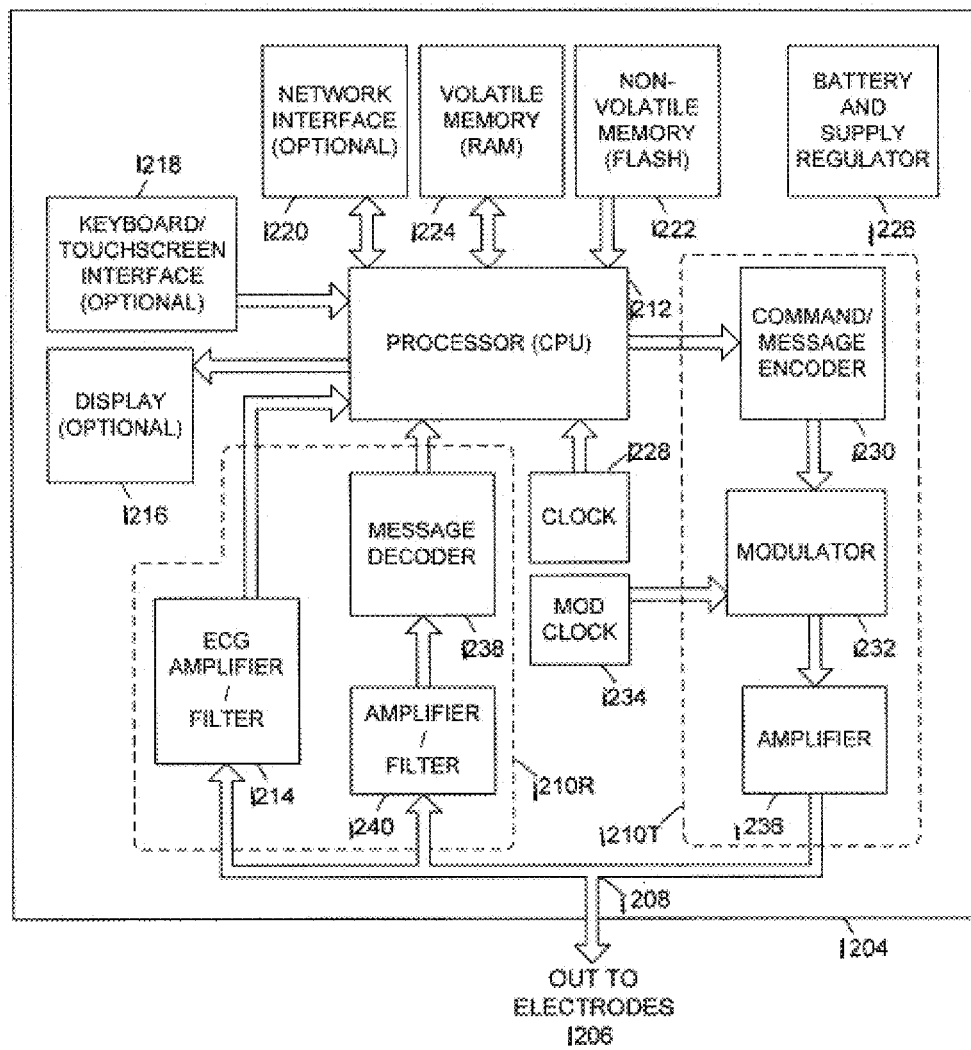
FIG. 8 is a schematic block diagram depicting an embodiment of an external programmer that can be used in a pacemaker system and adapted to communicate via conductive techniques.

Referring to FIG. 8, a schematic block diagram shows an embodiment of an external programmer 1204 adapted for communicating with an implanted pacemaker system using conducted communication. The external programmer 1204 comprises an interface 1208 configured for coupling to at least two electrodes 1206 that make electrical contact with body skin for communicating with one or more implanted pacemakers. The external programmer 1204 further comprises bidirectional communication pathways 1210R and 1210T coupled to the interface 1208 and configured for bidirectional communication with the one or more implanted pacemakers. The communication pathways comprise a receiving pathway 1210R that decodes information encoded on stimulation pulses generated by the one or more implanted pacemakers and conducted through body tissue.

The bidirectional communication pathways 1210R and 1210T are configured for communication with one or more leadless cardiac pacemakers via the electrodes 1206 and conduction through body tissue.

The external programmer 1204 can have bidirectional communication pathways 1210R and 1210T that further comprise a transmitting pathway 1210T that passes information from the programmer 1204 to one or more implanted pacemakers by conduction through the body tissue using modulation that avoids skeletal muscle stimulation.

In some arrangements, the bidirectional communication pathways 1210R and 1210T can be further specified to comprise a transmitting pathway that passes information from the programmer 1204 to the one or more implanted pacemakers by direct conduction using modulated signals at a frequency in a range from approximately 10 kHz to 100 kHz. Also in some arrangements, the two or more electrodes 1206 and the bidirectional communication pathways 1210R and 1210T can be configured for bidirectional information signal communication and for sensing an electrocardiogram.

Also in some embodiments, the bidirectional communication pathways 1210R and 1210T can further comprise a transmitting pathway 1210T that passes information from the programmer 1204 to multiple implanted devices in a common communication event. In some embodiments or selected operating conditions, the transmitting pathway 210T can be arranged to pass information from the programmer 1204 to multiple implanted devices in a common communication event whereby information specific to a single implanted device or a subset of implanted devices have a unique address assigned to the single implanted device or the subset of implanted devices and encoded in the information. The transmitting pathway 1210T can also be arranged to pass information from the programmer 1204 to multiple implanted devices in a common communication event whereby information designates a specific function that is executed by a particular implanted device or a particular subset of implanted devices. The information is passed to the multiple implanted devices without individual address information for activating execution by the particular implanted device or the particular subset of implanted devices alone. The transmitting pathway 1210T can also be arranged, either alone or in combination with other techniques, to pass information from the programmer 1204 to multiple implanted devices in a common communication event whereby information designates a specific function that is executed by a particular implanted device or a particular subset of implanted devices that comprise programming specific to the function adapted to recognize the received information is relevant to the function.

In the illustrative embodiment, the bidirectional communication pathways 1210R and 1210T comprise the two or more electrodes 1206 forming a conductive communication path between the programmer 1204 and the skin surface, and a transmitting pathway 1210T. The transmitting pathway 1210T comprises a processor 1212, a command/message encoder 1230, a modulator 1232, and an amplifier 1236. The processor 1212 is configured to communicate information to one or more implanted leadless cardiac pacemakers. The command/message encoder 1230 is coupled to the processor 1212 via a parallel interface and configured to encode and serialize data into a bit stream. Information encoding can be selected from encoding techniques such as on-off keying, frequency-shift keying, frequency modulation, and amplitude shift keying. The modulator 1232 is coupled to the command/message encoder 1230 and receives and modulates the serialized data using a frequency in a range from approximately 10 kHz to approximately 100 kHz. The amplifier 1236 is coupled to the modulator 1232 and increases signal amplitude to a level suitable for robust conducted communication.

The bidirectional communication pathways 1210R and 1210T further comprise a receiving pathway 1210R including a low-pass filter 1214 adapted to separate the electrocardiogram from the information signals.

In various embodiments and arrangements, the bidirectional communication pathways 1210R and 1210T further comprise a receiving pathway 1210R, that receives information at the programmer 1204 from the one or more implanted pacemakers by conduction through the body tissue. The receiving pathway 1210R can decode information, for example by decoding data that is encoded by the pacemakers using pacing pulse width, using binary-coded notches in a pacing pulse, using modulation of off-time between pacing pulses, or other suitable techniques for encoding data in the pacemakers.

In the illustrative embodiment, the bidirectional communication pathways 1210R and 1210T couple to the two or more electrodes 1206 forming a conductive communication path between the programmer 1204 and the skin surface, and a receiving pathway 1210R. The receiving pathway 210R comprises an electrocardiogram (ECG) amplifier/filter 1214, an analog-to-digital converter (ADC) which is not shown in FIG. 8, and the processor 1212. The electrocardiogram (ECG) amplifier/filter 1214 includes a differential band-pass amplifier configured to select and amplify signals in a frequency range from approximately 1 Hz to approximately 100 Hz. The analog-to-digital converter (ADC) is configured to digitize the filtered and amplified signal. The processor 1212 is coupled to the ADC and configured to receive and optionally display ECG data, and configured to decode information encoded into cardiac pacing pulses.

The programmer 1204 may further comprise a processor 1212 coupled to the bidirectional communication pathways and configured to manage communication with one or more pacemakers, for example leadless cardiac pacemakers. Leadless cardiac pacemakers can be implanted adjacent to an inside or an outside wall of a cardiac chamber as depicted in FIGS. 7A and 7B.

As depicted in FIG. 8, external electrodes 1206 enable a conductive communication path between the programmer 1204 and the skin surface. Electrocardiogram (ECG) signals enter an ECG amplifier/filter 1214, which can include a differential band-pass amplifier. In general, an ECG signal has spectral components in a range between 1 Hz and 100 Hz. Band-pass filter poles for the ECG amplifier/filter 1214 can be selected such that sufficient signal energy is passed within the 1 Hz to 100 Hz range, while filtering other signals that are not associated with cardiac activity. The ECG signal can be amplified and digitized using an analog-to-digital converter (ADC). Once digitized, the signal is passed to the processor, for example central processing unit (CPU) 212.

In some embodiments, the electrodes 1206 can be implemented with more than two electrodes to enable an electrocardiogram (ECG) to be sensed at multiple vectors and further to enable selection from among the multiple vectors for conducted communication with implanted leadless cardiac pacemakers so that system signal-to-noise ratio can be improved or maximized.

The CPU 1212 receives and optionally displays ECG data using a display interface 216 and can also display other data acquired from the implanted leadless cardiac pacemaker acquired through the encoded pacing pulses, such as battery voltage, lead impedance, sensed cardiac signal amplitude, or other system status information. The CPU 1212 also can accept input from a user via a keyboard and/or touch-screen interface 1218. Some examples of user input are selected pacing rate or pacing pulse amplitude for implanted leadless cardiac pacemakers. The CPU 1212 can also communicate over a network interface 1220 to other data entry or display units, such as a handheld computer or laptop/desktop unit. The network interface 1220 can be cabled or wireless and can also enable communication to a local area network or the internet for greater connectivity.

The processor 1212 is coupled to the bidirectional communication pathways and configured to perform one or more of various operations such as electrocardiogram sensing, retrieving status information from implanted pacemakers, modifying configuration parameters of multiple implanted pacemakers within a single or multiple cardiac cycles in information passed through a common electrode set, and other operations. A display interface 1216 coupled to the processor 212 can be configured to display an electrocardiogram sensed from the electrodes 1206. In some arrangements or embodiments, a secondary link 1220 can be coupled to the processor 1212 and configured for unidirectional or bidirectional wireless or cable transmission to and/or from a remote display and/or data-entry device to display an electrocardiogram sensed from the at least two electrodes, and/or to control the programmer and/or at least one implanted pacemaker.

The CPU 1212 can execute operations based on firmware stored in non-volatile memory (Hash) 1222. The non-volatile memory 1222 can also be used to store parameters or values that are to be maintained when power is removed. The CPU 1212 uses volatile memory or random access memory (RAM) 1224 as general storage for information such as ECG data, status information, swap memory, and other data. A battery and supply regulator 1226 gives a constant voltage supply to the programmer 1204 during normal operation. A clock module 1228 generates a system clock signal used by the CPU 1212 and by interface blocks for timing.

Figure 9:
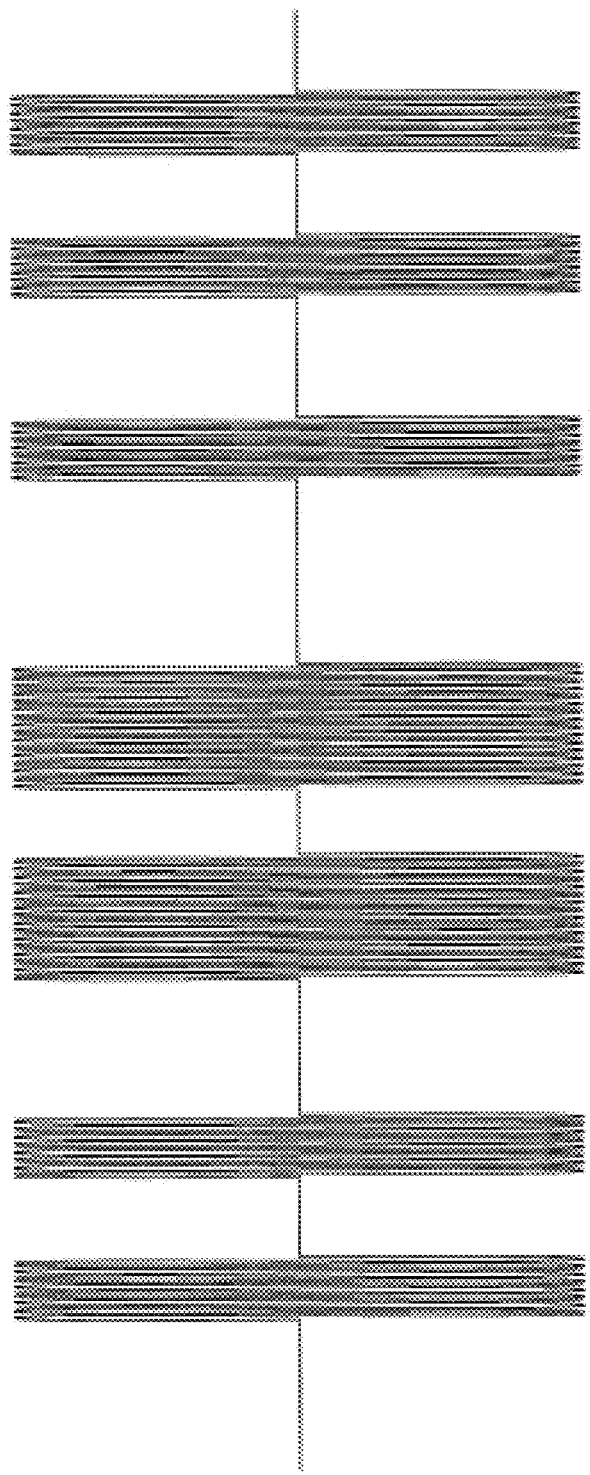
FIG. 9 is a time waveform graph showing a sample of modulated communication transmitted from an external programmer to a system of one or more leadless cardiac pacemakers.

The CPU 1212, during operation to communicate information to one or more implanted leadless cardiac pacemakers, sends the information over a parallel interface to a command/message encoder 1230, which serializes the data into a bit stream. Serialized data is sent to a modulator 1232. The serialized bit-stream is modulated, for example using a frequency between 10 kHz and 100 kHz. An optional separate modulator clock 1234 supplies a timing signal at a selected carrier frequency that may be used by the modulator 1232. An amplifier 1236 sets signal amplitude to a level that enables robust conducted communication. A sample of a modulated bit-steam is shown in FIG. 9 wherein logic high is shown as a medium high frequency sine wave. An encoding and modulation technique depicted in FIG. 9 is on-off keying. However, any other appropriate method whereby a modulated bit-stream can be generated at a medium high frequency may be used, for example frequency shift keying, frequency modulation, or amplitude shift keying.

Because multiple pacemaker devices can be implanted, communication of information from the programmer 1204 can be detected by all devices, enabling information to be sent to each implanted device without sending the same information multiple times.

If information for communication is specific to a single implanted device or a subset of devices, a unique address can be assigned to each device or subset. The address is encoded in the information sent to the plurality of devices, and any individual device can have the option to make use of information that either matches the address or the address of the subset to which the particular device belongs.

If each implanted device or a subset of devices performs a specific function which is different from other implanted devices, then information can be passed to the specific device or subset without the additional overhead of a group or individual address. For example, when the device or subset is responsible for only a specific function. When the programmer 1204 transmits information to the entire group, but the information is relevant to only the device or subset of that group, then any devices that cannot make use of the information may ignore the information as superfluous. The technique presumes that each device have unique programming specific to the associated function, and each device have capability to recognize whether or not received information is relevant to the function. Devices using the illustrative technique are not generic. The function of each device can be defined at the time of manufacture or at the time of implant or thereafter. The devices are labeled or marked such that the associated function can be known upon inspection.

To reduce the peak current for operation of the leadless cardiac pacemakers, a technique can be used in which a window or multiple windows occur between subsequent pacing pulses during which the leadless cardiac pacemaker does not charge pacing tank capacitor in preparation for the next pacing pulse. Instead the pacemaker enables an internal receiving amplifier. Because the programmer 1204 can sense pacing pulses from the implanted devices, the programmer 1204 can time data transmission to coincide with the predefined synchronous window or windows. A reduced peak current capability occurs because the charger and receiving amplifier, both power intensive elements, never have to be operated together. Because the data transmission is generally very short compared to the period between pacing pulses, the window technique should not significantly lower the ability of the leadless cardiac pacemaker to charge the pacing tank capacitor effectively between pacing pulses.

Referring again to FIG. 8, data acquired by the programmer 1204 from a specific implanted leadless cardiac pacemaker is received at the surface electrodes 1206 and passes to an amplifier/filter 1240, which functions to remove noise from the incoming signal. Any filtering performed by the amplifier/filter 1240 is designed to leave encoded pulses intact as much as possible. A message decoder 1238 determines whether the received signal is actually a pacing pulse or another signal, such as a cardiac R-wave.

Schemes can be implemented for transmitting data from the implant to the programmer that do not significantly increase the current consumption of the pacemaker. For example, the pacemaker could transmit data continuously in a loop, with no consumption penalty.

The method of encoding data using modulation of off-time between pacing pulses is less effective if pulses are inhibited, since data can be transmitted using only pacing pulses generated by the pacemaker. When data are encoded in binary-coded notches in the pacing pulse or by varying pacing pulse width, if a therapeutic pacing pulse is inhibited, then the leadless cardiac pacemaker can still generate a non-therapeutic pulse during the refractory period of the heart after the sensed beat, although the pacing pulse has the sole purpose of transmitting data to the programmer or optionally to at least one other implanted pacemaker.

Referring to FIGS. 10A-10E, schematic flow charts depict techniques that can be used in various embodiments of methods for communicating in an implantable pacemaker system. According to FIG. 10A, an illustrative method 700 comprises monitoring 702, at an external programmer, electrical signals conducted through body tissue to body surface electrodes and detecting 704 pulses generated by a body-implanted pacemaker. The external pacemaker decodes 706 information encoded into the generated pulse by the body-implanted pacemaker.

Figure 10A:
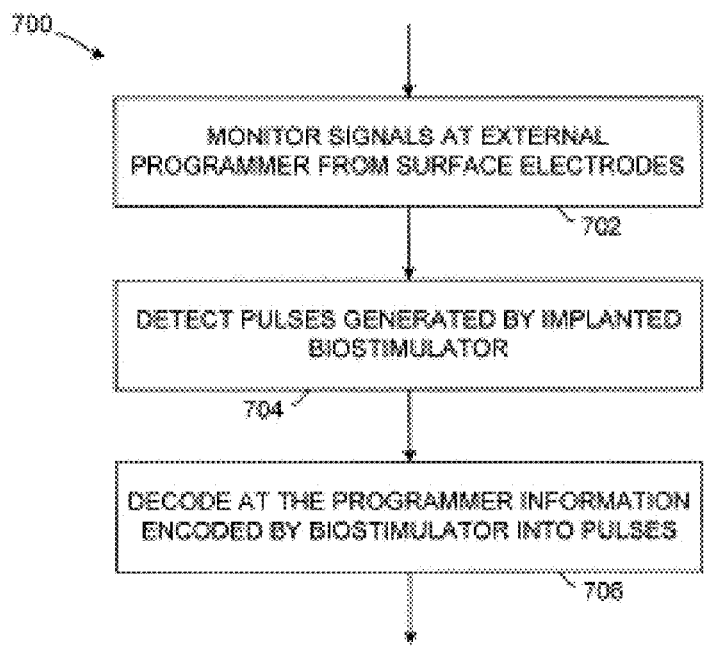
FIGS. 10A-10E are schematic flow charts depicting techniques that can be used in various embodiments of methods for communicating in an implantable pacemaker system.
Figure 10B:
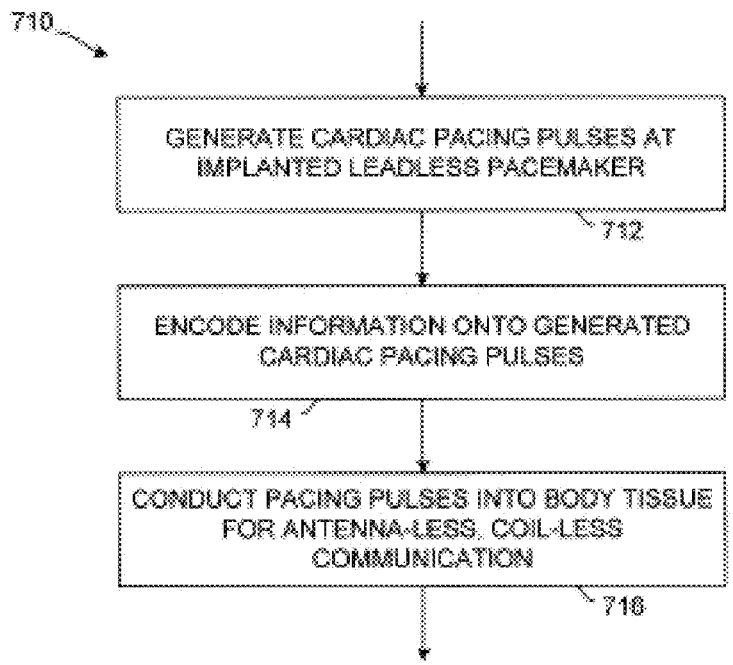

Referring to FIG. 10B, a method 710 can further comprise generating 712 cardiac pacing pulses at an implanted leadless cardiac pacemaker. Information is encoded 714 onto generated cardiac pacing pulses at the implanted leadless cardiac pacemaker by selective alteration of pacing pulse morphology that is benign to therapeutic effect and energy cost of the pacing pulse. In various embodiments, the implanted leadless cardiac pacemaker can encode the information using one or more techniques such as encoding using pacing pulse width, using binary-coded notches in a pacing pulse, and using modulation of off-time between pacing pulses. The cardiac pacing pulses are conducted 716 into body tissue via electrodes for antenna-less and telemetry coil-less communication. The information encoded onto generated cardiac pacing pulses can include pacemaker state information, battery voltage, lead impedance, sensed cardiac signal amplitude, pacemaker current drain, programmed parameters, and the like.

Figure 10C:
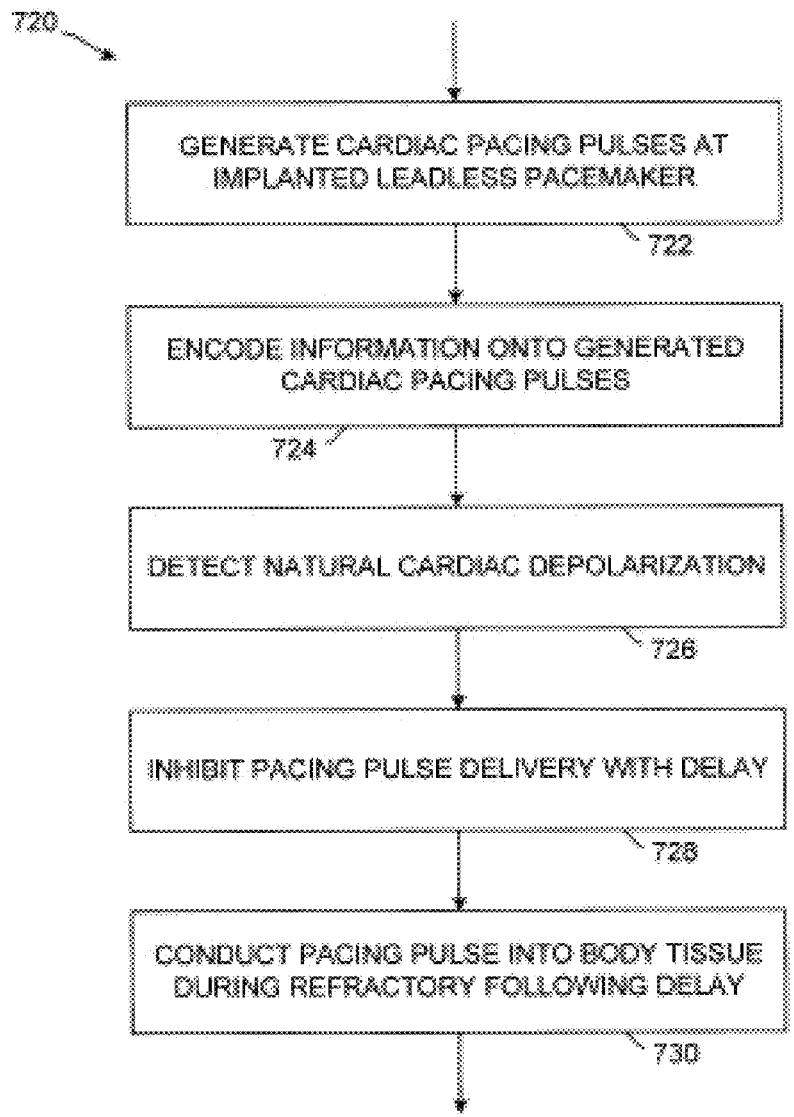

Referring to FIG. 10C, a method 720 can further comprise generating 722 cardiac pacing pulses at an implanted leadless cardiac pacemaker and encoding 724 information onto generated cardiac pacing pulses at the implanted leadless cardiac pacemaker by selective alteration of pacing pulse morphology that is benign to therapeutic effect and energy cost of the pacing pulse. The implanted leadless cardiac pacemaker detects 726 a natural cardiac depolarization and inhibits 728 cardiac pacing pulse delivery with delay for delivery during a refractory period following the natural cardiac depolarization. The cardiac pacing pulses are conducted 730 into body tissue via electrodes for antenna-less and telemetry coil-less communication.

Figure 10D:
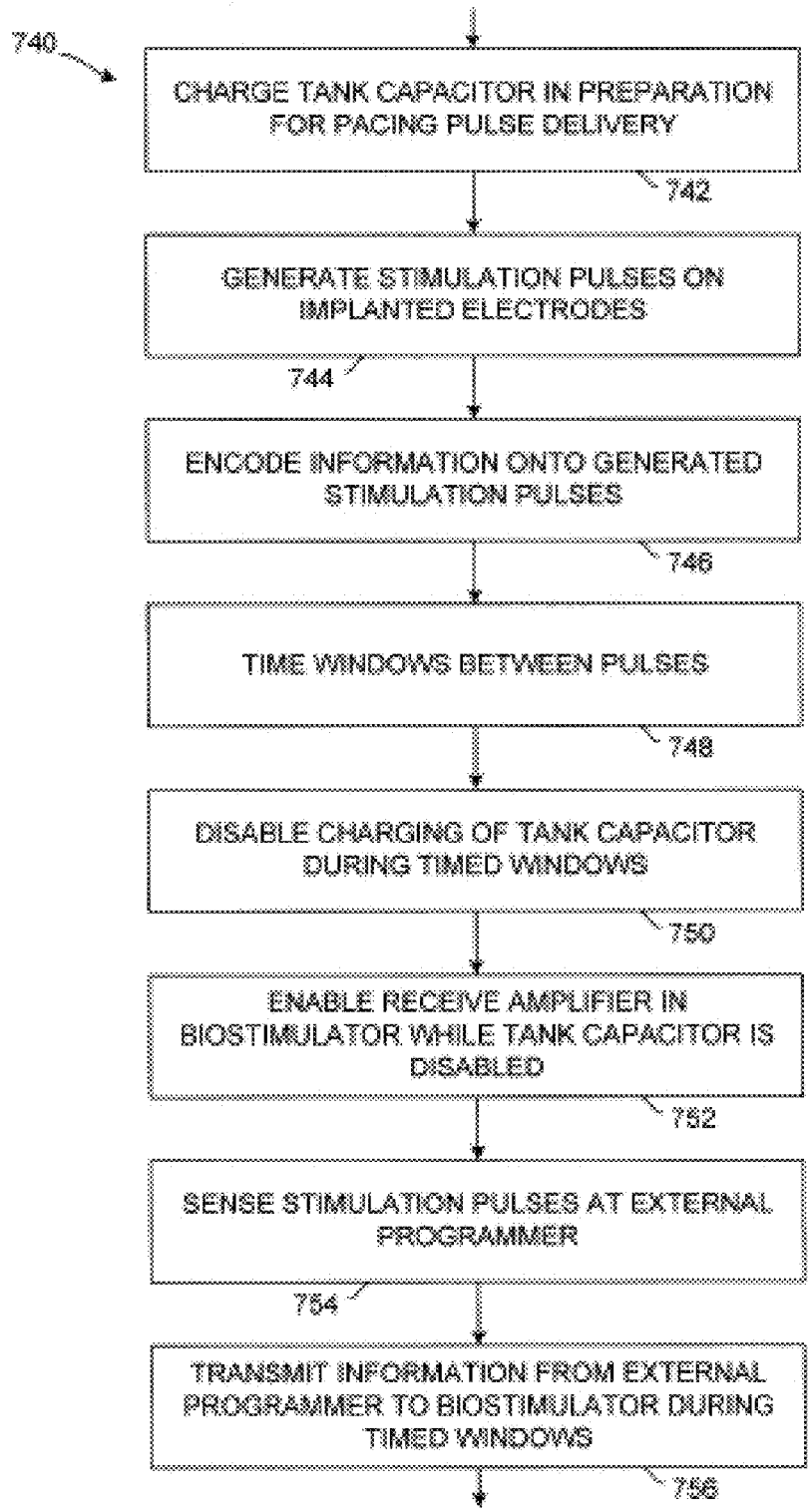

Referring to FIG. 10D, various embodiments of a method 740 can comprise charging 742 a tank capacitor in preparation for stimulation pulse generation. Stimulation pulses are generated 744 on stimulating electrodes of an implanted pacemaker and information encoded 746 onto generated stimulation pulses. One or more windows can be timed 748 between pulse generations. Charging of the tank capacitor is disabled 750 during the one or more timed windows and a receiving amplifier in the implanted pacemaker is enabled 752 while the tank capacitor is disabled. The external programmer senses 754 the stimulation pulses generated by the implanted pacemaker and transmits 756 information from the external programmer to the implanted pacemaker to coincide with the one or more timed windows. For example, the external programmer can detect a stimulation pulse from the implanted pacemaker, time a selected delay interval, and transmit data after the selected delay to coincide with a window that the implanted pacemaker's receive amplifier is enabled.

Figure 10E:
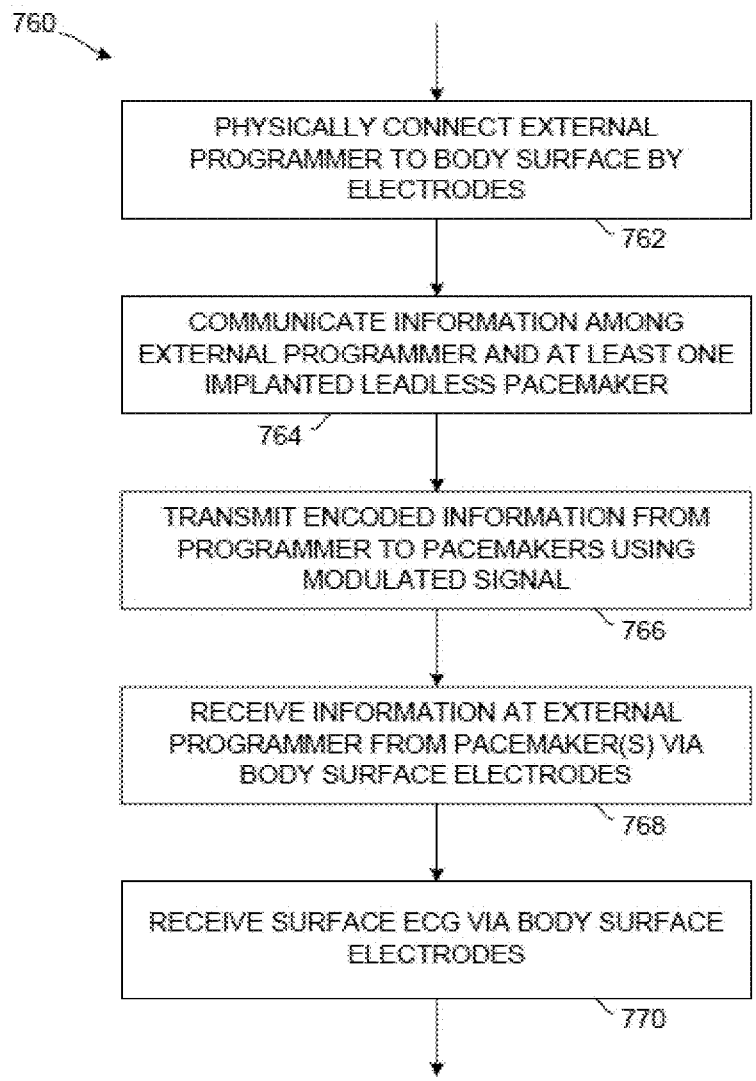

Referring to FIG. 10E, various embodiments of a method 760 can comprise physically connecting 762 the external programmer to a body surface via two or more body surface electrodes and communicating 764 information among the external programmer and one or more implanted leadless cardiac pacemakers. Encoded information is transmitted 766 from the external programmer to the implanted leadless cardiac pacemakers via the body surface electrodes using a modulated signal at a frequency in orange of approximately 10 kHz to approximately 100 kHz. The external programmer receives 768 the information via the body surface electrodes from one or more of the implanted leadless cardiac pacemakers by detecting information encoded into generated pacing pulses. The external programmer can also receive 770 a surface electrocardiogram via the body surface electrodes for display and analysis.

A person having ordinary skill in the art would understand that the communication mechanisms described herein with respect to communication with an external programmer 1104 can be used when the device 106 is a different type of device as well, for example when the device 106 is another pacemaker, a defibrillator, an implanted programmer, or an external programmer.

Specific Examples

Figure 11:
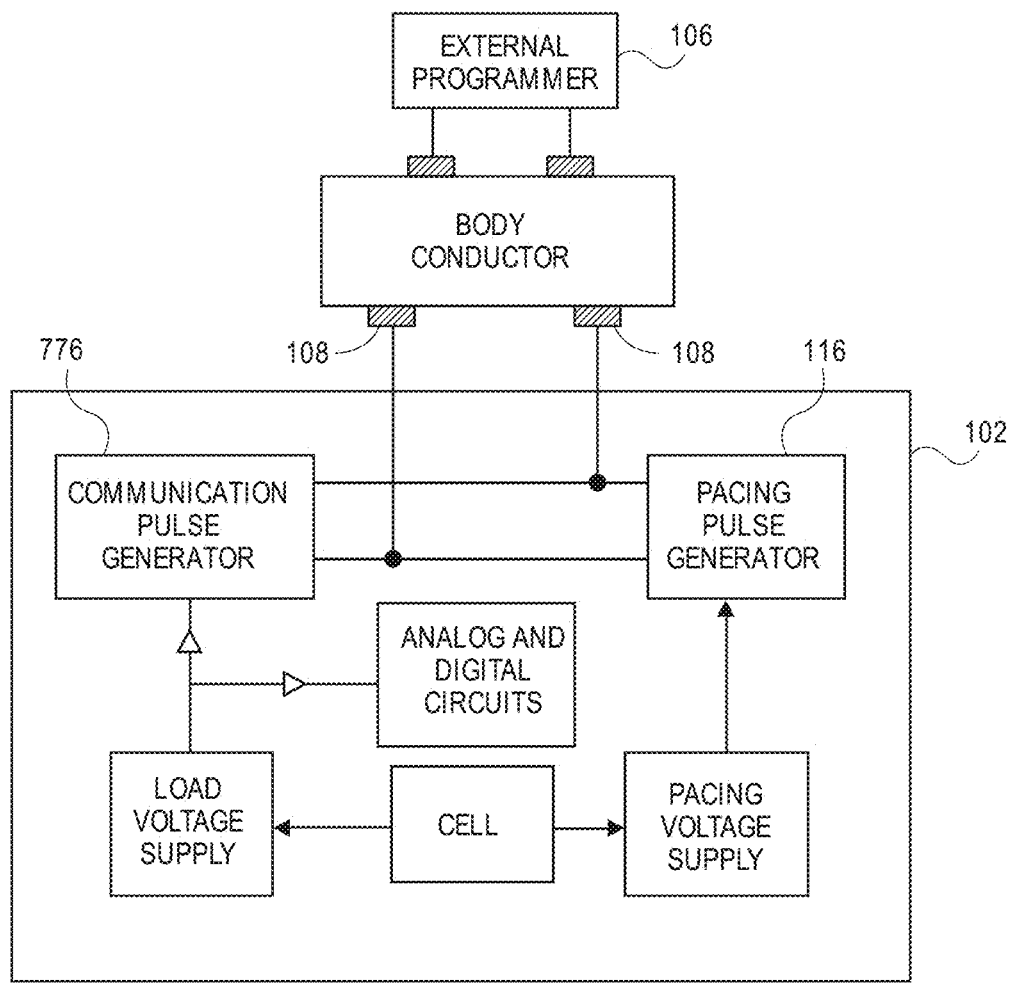
FIG. 11 is a schematic block diagram depicting an embodiment of an external programmer and a pacemaker having two pulse generators.

FIG. 11 illustrates one embodiment including an external programmer 106 in communication with at least one cardiac pacemakers 102, the pacemaker 102 including a first pulse generator 116 and a second pulse generator 776. The first pulse generator 116 can be used for pacing through the electrodes 108 while the second pulse generator 776 can be used for delivering communication pulses through the electrodes 108 to the external device 106. Thus, the second pulse generator 776 can be uninvolved in the pacing process. The second pulse generator 776 can generate different pulses at different amplitudes from the first pulse generator 112. Advantageously, this allows for the amplitude of the pulses to be optimized for communication or for pacing.

The second pulse generator 776 can be powered from a power supply shared with another function. This power supply can be the lowest-voltage supply already used for another function. For example, the second pulse generator 776 can use the power supply used for analog and digital circuits, which operates at approximately 1.5V. Using a low-voltage supply permits generating more pulses per transmitted signal for the same power consumption, which in turn provides a more narrow-band transmitted frequency spectrum, thereby improving the signal-to-noise ratio at the receiver of the external device 106. By sharing the power supply for the pulse generator 776 with another function, the component count can remain low and the pacemaker size small.

In some embodiments, the pacemaker 102 can transmit communication pulses at the lowest frequency f such that root-mean-square (RMS) transmitted current presents no risk for arrhythmia induction. International standards permit current in cardiac electrodes of up to 10 uArms*f/1 kHz. Therefore, the frequency of the transmitted signal of the cardiac pacemaker 102 can be approximately equal to the current*$10^8$ Hz/A. For example, a square wave at 1.5V peak, the voltage discussed above, with a load resistance of 0.6 KΩ, typical for cardiac electrodes, provides 2.5 mArms. Accordingly, to meet international standards, the frequency of the transmitted pulses can be greater than or equal to 0.25 MHz. Thus, in one embodiment, the pacemaker 102 described herein can transmit communication pulses at a frequency close to 0.25 MHz, e.g., between 0.25 MHz and 0.5 MHz. The selection of the lowest frequency signal such that the RMS transmitted current presents no risk for arrhythmia induction, as described herein, provides a design advantage because lower frequencies are less affected by parasitic and intended low pass filters associated with protection and interference suppression circuitry.

Like the pacemaker 102, in some embodiments, the external device 106 can transmit communication pulses to the pacemaker at the lowest frequency f such that the RMS transmitted current presents no risk for arrhythmia induction or sensation. International standards permit current in skin electrodes of 0.1 mArms*f/1 kHz. Therefore, the frequency of the transmitted signal of the external device 106 can be approximately equal to the current*$10^7$. In one embodiment, the external device 106 transmits communication pulses to the pacemaker 102 using a biphasic square wave with approximately a 25 Volt peak. Advantageously, 25 Volts provides approximately the largest voltage that can be transmitted through skin electrodes at a 0.25 MHz frequency that is safe. A square wave at 25 V peak with a load resistance of 0.6 KΩ, typical for skin electrodes, provides 25 mArms. Accordingly, to meet international standards, the frequency of the transmitted pulses can be greater than or equal to 0.25 MHz. Therefore, in one embodiment, the external device 106 can transfer the communication signal at around 0.25 MHz, such as between 0.25 and 0.5 MHz. Use of the lower frequency in this range advantageously ensures that the communication signal will be less affected by parasitic and intended low pass filters required for protection and interference suppression circuitry. Further, an amplifier that is responsive to lower frequency signals generally requires less current and enables a longer-lived or smaller pacemaker 102.

In some embodiments, the external device 106 can have a receiving filter centered at the fundamental frequency of transmitted pulses of the pacemaker 102. Accordingly, the external device 106 can reject interference signals outside of this band, such as signals applied to patients by commercial electrocardiographs for confirming surface electrode contact or unintentional radiation from switching power supplies.

Further, referring to FIGS. 12 and 13, a frequency of greater than 200 kHz allows for possible increase in transmission amplitude by providing some additional options for compliance with standards. FIGS. 12 and 13 summarize international standards applicable to the programmer's body electrode current. These figures show that above 200 kHz the hazard presented by the programmer's carrier current, called "patient auxiliary current" by the standards, is limited to thermal considerations rather than arrhythmia induction and sensation that can occur at lower frequencies. Consequently, the limit for body electrode current above 200 kHz can be increased simply by increasing the surface area of the programmer's body electrodes.

Finally, the programmer's transmitted carrier frequency can be selected to be an integral multiple of the implant's clock frequency, on that an integral number of programmer carrier pulses fall within a period of the implant's clock. This allows the programmer to adjust the timing and count of its transmitted pulses for exact alignment to timing windows in the implant, which are set by the implant's clock.

In some embodiments, the pacemaker 102 can transmit communication pulses to the external device 106 during the pacemaker's absolute refractory period. Doing so advantageously ensures that the transmission does not interfere with heartbeat sensing and that the induction of arrhythmias is prevented. Signals can be transmitted only during the absolute refractory period, as the refractory period is sufficiently long to permit full transmission of such signals in place of those encoded in a pacing pulse or in a refractory pulse triggered by sensing. Alternatively, signals can be transmitted during the absolute refractory period in addition to being encoded in a pacing pulse or in a refractory period triggered by sensing, which advantageously increases the data rate of the signal.

Similarly, in some embodiments, the external device 106 can transmit communication pulses to the pacemaker 102 during the pacemaker's absolute refractory period. The external device 106 can transmit communication only during the refractory period. Advantageously, in the case where the programmer is transmitting communication pulses to the pacemaker 102 only during the refractory period, the pacemaker 102 can disconnect its input capacitor used for protection against electromagnetic interference (EMI) during the refractory period only, thereby allowing the pacemaker 102 to more effectively receive the high-frequency communication pulses from the external device 106 while maintaining protection from EMI during the rest of the pacing cycle.

In some embodiments, the pacemaker 102 charge-balances transmitted communication pulses before the end of the pacemaker's absolute refractor period so that the residual unbalanced current does not interfere with heart beat sensing. To do this, the pacemaker 102 can transmit monophasic communication pulses and provide the charge balancing using a fastdischarge circuit already provided for balancing monophasic pacing pulses. Alternatively, the pacemaker 102 can transmit biphasic communication pulses in such a way that each phase balances the other. Charge-balancing biphasic communication signals advantageously permits the pacemaker 102 to transmit more signals in a period of time than when using monophasic communication pulses because it is not necessary to reserve time in the refractory period for an additional balancing pulse.

In some embodiments, when not communicating with the external device 106, the pacemaker 102 can send a "bell-ringer" signal to the external device and listen for a response during at least one window timed from the bell-ringer signal. For example, the implant can send a pulse to the programmer once every five pacing cycles, and then listen for a response in a short window, such as 1 millisecond or less in duration, at a predetermined time, such as 32 milliseconds, after sending the bell-ringer pulse. The pacemaker 102 can send a belt-ringer at the start of every Nth pacing cycle, with N selected in the range from 1 to 20, such as from 3 to 7, to optimize the pacemaker's power consumption (which decreases with N) and the latency for initiating communication (which increases with N). The pacemaker's communication receiving amplifier can then be powered down outside of the window. This infrequent transmission and reception of communication signals can advantageously reduce the amount of power consumption of the pacemaker 102, thereby increasing its longevity and/or reducing the overall size of the pacemaker 102.

In some embodiments, when communicating with the external device 106, the pacemaker 102 can send a synchronization signal to the external device 106 and then send additional signals and/or listen for a response during at least one window timed from the synchronization signal. In addition to signaling the upcoming transfer of information, the synchronization signal can transfer additional information as well, including event markers, event counters, and sensor output. The frequency, number, and duration of these signals and windows can be chosen to optimize the pacemaker's power consumption (which decreases with decreasing frequency, number, and duration) and the communicated data range (which increases with these parameters). For example, the pacemaker can transmit an event marker along with a synchronization pulse for negligible additional power consumption. Further, the message coding can be arranged such that the data most frequently sent requires fewer transmitted pulses and shorter receiving windows. For example, the event marker for a pacing pulse can comprise two bits, both with data value zero and therefore no transmitted pulse, thereby further reducing the pacemaker's power consumption.

In some embodiments, the pacemaker 102 or external device 106 can measure the time between received communication pulses. Measuring the time between received communication pulses can allow the pacemaker 102 or external device 106 to estimate the other devices' clock frequency and therefore optimize the timing of its transmitted pulses and receiving windows accordingly.

In some embodiments, the pacemaker 102 or external device 106 can initiate communication automatically when the user applies skin electrodes and connects them to the external device.

In some embodiments, when communicating, the pacemaker 102 or external device 106 can measure the peak, average, integrated, or filtered amplitude of the received signal to set an automatic discriminating threshold for noise rejection.

Power Requirements

With regard to operating power requirements in the leadless cardiac pacemaker 102, for purposes of analysis, a pacing pulse of 5 volts and 5 milliamps amplitude with duration of 500 microseconds and a period of 500 milliseconds has a power requirement of 25 microwatts.

In an example embodiment of the leadless pacemaker 102, the processor 112 typically includes a timer with a slow clock that times a period of approximately 10 milliseconds and an instruction-execution clock that times a period of approximately 1 microsecond. The processor 112 typically operates the instruction-execution clock only briefly in response to events originating with the timer, communication amplifier 134, or cardiac sensing amplifier 132. At other times, only the slow clock and timer operate so that the power requirement of the processor 112 is no more than 5 microwatts.

For a pacemaker that operates with the aforementioned slow clock, the instantaneous power consumption specification, even for a commercially-available micropower microprocessor, would exceed the battery's power capabilities and would require an additional filter capacitor across the battery to prevent a drop of battery voltage below the voltage necessary to operate the circuit. The filter capacitor would add avoidable cost, volume, and potentially lower reliability.

For example, a microprocessor consuming only 100 microamps would require a filter capacitor of 5 microfarads to maintain a voltage drop of less than 0.1 volt, even if the processor operates for only 5 milliseconds. To avoid the necessity for such a filter capacitor, an illustrative embodiment of a processor can operate from a lower frequency clock to avoid the high instantaneous power consumption, or the processor can be implemented using dedicated hardware state machines to supply a lower instantaneous peak power specification.

In a pacemaker, the cardiac sensing amplifier typically operates with no more than 5 microwatts.

An accelerometer amplifier, or other general purpose signal conditioning amplifier, operates with approximately 10 microwatts.

A communication amplifier at 100 kHz operates with no more than 25 microwatts. The battery ammeter and battery voltmeter operate with no more than 1 microwatt each.

A pulse generator typically includes an independent rate limiter with a power consumption of no more than 2 microwatts.

The total power consumption of the pacemaker is thus 74 microwatts, less than the disclosed 75-microwatt battery output.

Improvement attained by the illustrative cardiac pacing system 100 and leadless cardiac pacemaker 102 is apparent.

The illustrative cardiac pacing system 100 enables encoding optional outgoing communication in the pacing pulse, so that the outgoing communication power requirement does not exceed the pacing current requirement, approximately 25 microwatts.

The illustrative leadless cardiac pacemaker 102 can have sensing and processing circuitry that consumes no more than 10 microwatts as in conventional pacemakers.

The described leadless cardiac pacemaker 102 can have an incoming communication amplifier for receiving triggering signals and optionally other communication which consumes no more than 25 microwatts.

Furthermore, the leadless cardiac pacemaker 102 can have a primary battery that exhibits an energy density of at least 0.5 watt-hours per cubic centimeter (W·h/cc), for example at least 1 W·h/cc, such as at least 3 W·h/cc.

Use of conducted communication of information improves over standard methods of communication in several aspects. For example, the illustrative conductive communication also enables power consumption to be reduced due to substantially lower current requirements and eliminating peak power demands currently imposed by existing inductive and radio frequency (RF) systems. Also, the conductive communication technique uses elements generally already existing in the implanted pulse generator, such as the therapeutic electrodes that function as an input-output device, enabling elimination of a coil or antenna that are conventionally used for communication and reducing complexity and component count significantly.

Terms "substantially", "essentially", or "approximately", that may be used herein, relate to an industry-accepted tolerance to the corresponding term. Such an industry-accepted tolerance ranges from less than one percent to twenty percent and corresponds to, but is not limited to, component values, integrated circuit process variations, temperature variations, rise and fall times, and/or thermal noise. The term "coupled", as may be used herein, includes direct coupling and indirect coupling via another component, element, circuit, or module where, for indirect coupling, the intervening component, element, circuit, or module does not modify the information of a signal but may adjust its current level, voltage level, and/or power level. Inferred coupling, for example where one element is coupled to another element by inference, includes direct and indirect coupling between two elements in the same manner as "coupled".

While the present disclosure describes various embodiments, these embodiments are to be understood as illustrative and do not limit the claim scope. Many variations, modifications, additions and improvements of the described embodiments are possible. For example, those having ordinary skill in the art will readily implement the steps necessary to provide the structures and methods disclosed herein, and will understand that the process parameters, materials, and dimensions are given by way of example only. The parameters, materials, and dimensions can be varied to achieve the desired structure as well as modifications, which are within the scope of the claims. Variations and modifications of the embodiments disclosed herein may also be made while remaining within the scope of the following claims. Phraseology and terminology employed herein are for the purpose of the description and should not be regarded as limiting. With respect to the description, optimum dimensional relationships for the component parts are to include variations in size, materials, shape, form, function and manner of operation, assembly and use that are deemed readily apparent and obvious to one of ordinary skill in the art and all equivalent relationships to those illustrated in the drawings and described in the specification are intended to be encompassed by the present description. Therefore, the foregoing is considered as illustrative only of the principles of structure and operation. Numerous modifications and changes will readily occur to those of ordinary skill in the art whereby the scope is not limited to the exact construction and operation shown and described, and accordingly, all suitable modifications and equivalents may be included.

What is claimed is:

1. A leadless pacemaker for pacing a heart of a human comprising:
    a hermetic housing;
    at least two electrodes on or near the hermetic housing, the at least two electrodes configured to deliver energy to stimulate the heart and to transfer communication information to or from at least one external device; and
    a pulse generator in the housing, the pulse generator configured to provide energy to the at least two electrodes and to transfer the communication information through the at least two electrodes to the external device.

2. The leadless pacemaker of claim 1, wherein the external device is a second leadless pacemaker, a defibrillator, a conventional pacemaker, an implanted programmer, or a programmer external to the body of the human.

3. The leadless pacemaker of claim 1, wherein the information is encoded in sub-threshold pulses.

4. The leadless pacemaker of claim 1, wherein the pulse generator further comprises a stimulation pulse generator in the housing, wherein the stimulation pulse generator is configured to provide energy to the at least two electrodes to stimulate the heart.

5. The leadless pacemaker of claim 1, further comprising a controller in the hermetic housing, the controller configured to communicate with the external device by transferring the information through the at least two electrodes.

6. The leadless pacemaker of claim 5, wherein the controller is configured to communicate with the external device by transferring the information through the at least two electrodes during a pacing pulse.

7. The leadless pacemaker of claim 5, wherein controller is configured to communicate with the external device by transferring the information through the at least two electrodes outside of a refractory period or pacing pulse.

8. The leadless pacemaker of claim 5, wherein the controller is configured to communicate with the external device by transferring the information through the at least two electrodes only during an absolute refractory period.

9. The leadless pacemaker of claim 5, wherein the controller is configured to provide charge balancing of the information before the end of a refractory period.

10. The leadless pacemaker of claim 5, wherein the controller is configured to transfer information to or from the external device by sending a bell-ringer signal to the external device and listening for a response from the external device only during a set time period after the bell-ringer signal.

11. The leadless pacemaker of claim 5, wherein the controller is configured to send a synchronization signal through the at least two electrodes to the external device to start transfer of a part of the information.

12. The leadless pacemaker of claim 5, wherein the controller is configured to measure a length of time between encoded information signals received by the at least two electrodes.

13. The leadless pacemaker of claim 12, wherein the controller is configured to use the measured length of time to estimate a clock frequency of the external device and optimize the timing of the transfer of information.

14. The leadless pacemaker of claim 1, further comprising a sensing amplifier to receive and amplify signals received by the, at least two electrodes, wherein the pacemaker is configured to discriminate signals received by the at least two electrodes for noise rejection.

15. A system for pacing a heart of a human comprising:
    an external device; and
    a leadless pacemaker comprising a hermetic housing, a pulse generator in the hermetic housing and at least two electrodes on the hermetic housing, the pulse generator configured to provide pacing pulses to the at least two electrodes to stimulate the heart and to transfer communication pulses through the at least two electrodes to provide communication information to the external device, wherein the eternal device is not attached to the leadless pacemaker, and wherein the at least two electrodes are configured to deliver the pacing pulses to stimulate the heart and to transfer the communication pulses to the external device.

16. The system of claim 15, wherein the communication pulses include sub-threshold pulses.

17. The system of claim 15, wherein the external device is a second leadless pacemaker, a defibrillator, a conventional pacemaker, an implanted programmer, or a programmer external to the body of the human.

18. The system of claim 17, wherein the external device is a programmer external to the body of the human, and wherein the programmer comprises at least two skin electrodes configured to attach to skin of the human, the at least two skin electrodes further configured to transfer the communication pulses to or from the leadless pacemaker.

19. The system of claim 18, wherein the external device further comprises a controller, the controller configured to communicate with the leadless pacemaker by transferring the communication pulses through the at least two skin electrodes.

20. The system of claim 19, wherein the controller is configured to transmit the communication pulses through the at least two skin electrodes using a biphasic square wave.

21. The system of claim 20, wherein the biphasic square wave has approximately a 25V peak amplitude.

22. The system of claim 15, wherein the external device further comprises a controller, the controller configured to communicate with the leadless pacemaker by transferring the communication pulses to or from the leadless pacemaker.

23. The system of claim 22, wherein the controller is configured to transfer the communication pulses during a pacing pulse.

24. The system of claim 22, wherein the controller is configured to transfer the communication pulses outside of a refractory period or pacing pulse.

25. The system of claim 22, wherein the controller is configured to transfer the communication pulses only during an absolute refractory period.

26. The system of claim 20, wherein the controller is configured to measure a length of time between the communication pulses transferred from the leadless pacemaker.

27. The system of claim 26, wherein the controller is configured to use the measured length of time to estimate a clock frequency of the leadless pacemaker and optimize the timing of the transfer of the communication pulses.

28. The system of claim 15, wherein the external device further comprising a sensing amplifier to receive and amplify the, communication pulses, and wherein the external device is configured to discriminate the communication pulses transferred from the leadless pacemaker for noise rejection.

29. A method of pacing a heart of a human, comprising:
providing a leadless pacemaker comprising a hermetic housing, a pulse generator in the hermetic housing and at least two electrodes on the hermetic housing;
configuring the pulse generator to provide pacing pulses and communication pulses to the at least two electrodes;
delivering the pacing pulses through the at least two electrodes of the leadless pacemaker to stimulate the heart; and
communicating the communication pulses between the at least two electrodes and an external device not attached to the leadless pacemaker.

30. The method of claim 29, wherein communicating occurs only during a refractory period.

31. The method of claim 29, wherein communicating occurs outside of a refractory period the pacing pulses.

32. The method of claim 29, further comprising charge balancing the communication pulses before the end of a refractory period.

33. The method of claim 29, wherein communicating occurs only during predetermined times in one or more pacing cycles.

34. The method of claim 29, further comprising sending a synchronization signal through the at least two electrodes to the external device to start transfer of a part of the communication pulses.

* * * * *